(12) United States Patent
Webler

(10) Patent No.: US 8,708,954 B2
(45) Date of Patent: Apr. 29, 2014

(54) AGENT DELIVERY CATHETERS

(75) Inventor: William E. Webler, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 1116 days.

(21) Appl. No.: 12/553,036

(22) Filed: Sep. 2, 2009

(65) Prior Publication Data

US 2010/0057037 A1    Mar. 4, 2010

Related U.S. Application Data

(60) Provisional application No. 61/093,701, filed on Sep. 2, 2008.

(51) Int. Cl.
*A61M 37/00* (2006.01)
*A61M 31/00* (2006.01)
*A61M 25/00* (2006.01)

(52) U.S. Cl.
USPC ......... 604/95.04; 604/525; 604/528; 604/510

(58) Field of Classification Search
USPC .............. 604/101.01, 101.03, 96.01, 528, 604/101.05, 103.02, 95.04, 525, 500, 510
See application file for complete search history.

(56) References Cited

U.S. PATENT DOCUMENTS

| 5,741,429 A | 4/1998 | Donadio et al. |
| 6,352,531 B1 | 3/2002 | O'Connor et al. |
| 6,855,124 B1 | 2/2005 | Gonzalez et al. |
| 2004/0243102 A1 | 12/2004 | Berg et al. |
| 2007/0129792 A1 | 6/2007 | Picart et al. |

FOREIGN PATENT DOCUMENTS

| DE | 41 04 092 | 8/1991 |
| JP | 06-227296 | 8/1994 |
| JP | 2007-500756 A | 1/2007 |
| JP | 2007-503840 A | 3/2007 |
| WO | WO 2004/110270 | 12/2004 |
| WO | WO 2005/021730 | 3/2005 |
| WO | WO 2006/122147 | 11/2006 |
| WO | WO 2007/108775 | 9/2007 |

OTHER PUBLICATIONS

International Search Report for PCT/US2009/055784, mailed 3/29/10, 12 pgs.
Veerabadran et al. "Nanoencapsulation of Stem Cells within Polyelectrolyte Multilayer Shells" Macromolecular Bioscience, vol. 7, pp. 877-882 (2007).
Yim et al., "Proliferation and differentiation of human mesenchyma stem cell encapsulated in polyelectrolyte complexation fibrous scaffold", Biomaterials, vol. 27, pp. 6111-6122 (2006).

(Continued)

*Primary Examiner* — Kami A Bosworth
*Assistant Examiner* — Imani Hayman
(74) *Attorney, Agent, or Firm* — Squire Sanders (US) LLP

(57) ABSTRACT

An agent delivery catheter that includes an anti-whipping feature, improved assembly of distal parts and/or accuracy/repeatability of needle delivery to a target tissue. Additional features include fitting a catheter with a pneumatic delivery device for delivery of a therapeutic agent without using a needle.

19 Claims, 15 Drawing Sheets

(56) References Cited

OTHER PUBLICATIONS

Translation of the Japanese Notice of Reasons for Rejection dispatched by JPO on May 14, 2014, in connection with Appl. No. P2011-525299, 4 pgs.

Translation of the Notice of Reasons for Rejection issued by JPO for appl. No. P2011-525297, dispatched Aug. 20, 2013, 3 pgs.

Akira Ito et al., "Tissue Engineering Using Magnetite Nanoparticles and Magnetic Force: Heterotypic Layers of Cocultured Hepatocytes and Endothelial Cells", Tissue Engineering vol. 10, No. 5/6 pp. 833-840 (2004).

Veerabadran et al., "Nanoencapsulation of Stem Cells within Polyelectrolyte Multilayer Shells", Micromol. Biosci 7, pp. 877-882 (2007).

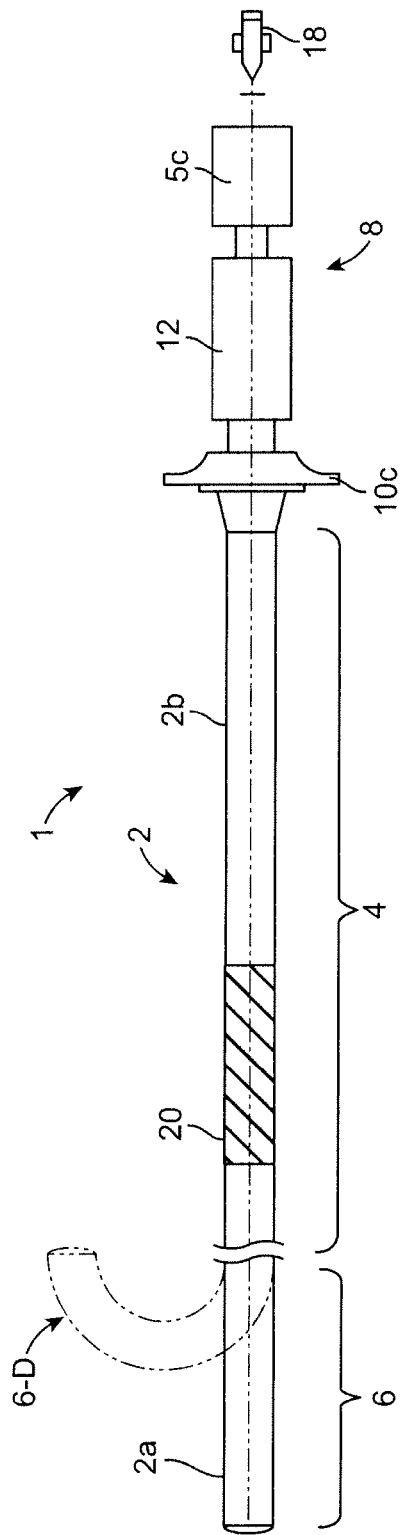
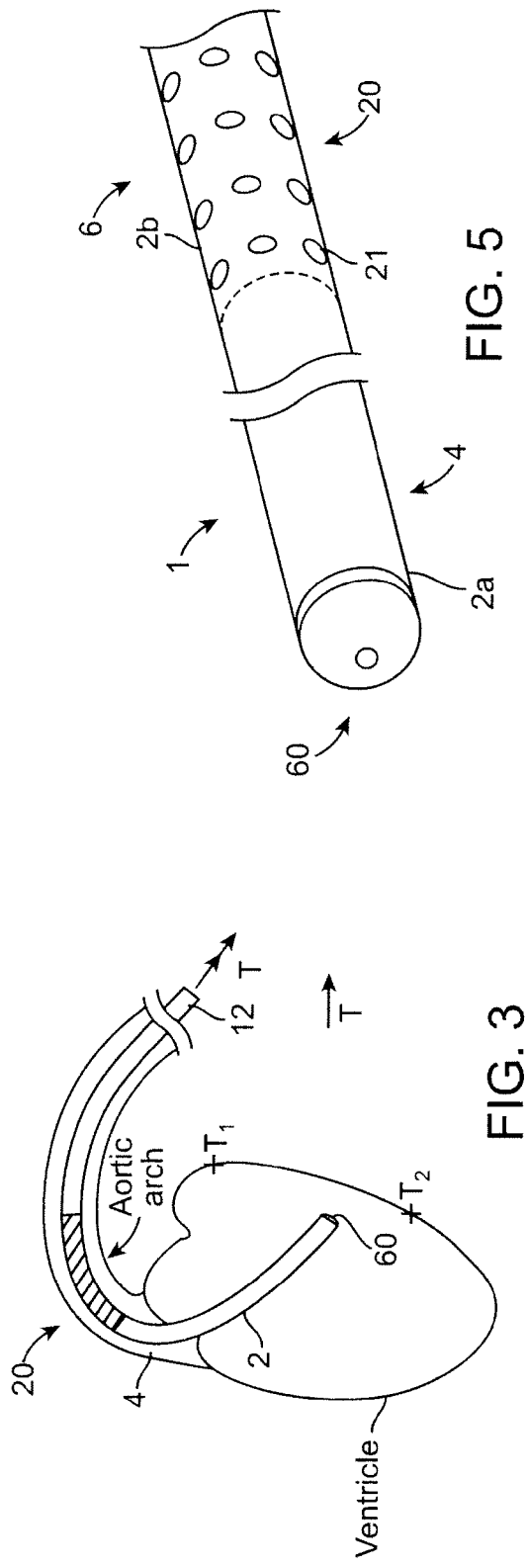
FIG. 2
FIG. 5
FIG. 3

Oval ID
and OD

Circular OD,
Oval ID

Oval OD,
Circular ID

Triangular ID
and OD

Circular OD,
Triangular ID

Triangular OD,
Circular ID

AGENT DELIVERY CATHETERS

PRIORITY STATEMENT

This application claims priority under 35 U.S.C. §119(e) to U.S. Provisional Application No. 61/093,701 filed Sep. 2, 2008.

BACKGROUND OF THE INVENTION

1. Field of the Invention

The present invention relates to medical devices; more particularly, this invention relates to catheters and in particular agent delivery catheters.

2. Background of the Invention

Steerable catheters have been commonly used in applications such as mapping (e.g., cardiac mapping), drug delivery (e.g., intramyocardial drug delivery), and ablation, (e.g., arrhythmia ablation).

A steerable catheter has a deflectable, flexible distal section and a stiffer proximal shaft. Locating a tip of a steerable catheter in three-dimensional space during a medical procedure involves three distinct modes of operation for the catheter: translational catheter movement along the shaft direction, deflection of the flexible distal section, and turning of the catheter shaft to direct the deflection toward a target therapy site. A tendon wire is included to control the deflection of the distal section. This tendon wire is located inside of a sheath running along and within the catheter shaft with its distal end attached near the distal tip of the catheter. A pulling mechanism is included within the proximal catheter handle, which is coupled to the proximal end of the catheter shaft. The pulling mechanism controls the tendon wire to deflect the distal section of the catheter shaft. Radially, the tendon wire is located off-center of the catheter shaft center to create a moment toward the intended deflection side in the catheter distal deflectable section. When the tendon wire is pulled, the catheter deflects toward the radial direction to which the tendon wire is located. The deflection section is typically made to be much more flexible than the rest of the catheter shaft. When the tendon wire is pulled in tension, the catheter shaft wants to "curl up." The distal section is the most flexible section of the catheter shaft and thus it deflects when the tendon wire is pulled. To direct the deflected section toward the target site, an operator turns the catheter shaft on the proximal end. The deflection section responds to the torque in a fashion that is governed by the way the catheter is constructed.

One problem commonly occurring in the working of this kind of catheter is that the catheter whips when rotated from the proximal end of the shaft. Whipping is caused by the resistance of the catheter to turn away from its preferred orientation. This whipping problem gets further magnified when the catheter distal section is deflected and/or when the catheter is resident in tortuous vasculature.

There is a need to improve upon catheter shaft design so that it can exhibit more beneficial torque response without significant whipping, i.e., controlled whipping. This will provide the physician with more ability to aim the catheter tip, which can lead to improved delivery accuracy and treatment outcome.

Agent delivery catheters have been proposed for treating conditions relating to congestive heart failure. This disease progresses cyclically, the cause being overcompensation of the heart muscle to make up for the loss of function from infracted myocardium. As the heart continues to overcompensate, more tissue becomes infracted, and the heart grows in size until the anatomical valve structures can no longer operate as intended. The resulting complications become extremely serious. Existing methods for treating congestive heart failure include the removal of infarct tissue and the constraint of the heart muscle.

Another approach for treating infarct myocardial tissue is the implantation of cells, such as mesenchymal stem cells, skeletal myoblasts, bone marrow mononuclear cells, etc., which will facilitate the revitalization of the infracted heart tissue. Hereafter, these types of materials, as well as solutions containing them, will be referred to as therapeutic agents.

Delivery of the therapeutic agents has generally required that a needle puncture the myocardial tissue prior to delivering a bolus of therapeutic agent through a needle lumen into the tissue. Multiple punctures may be required, and each puncture causes some amount of tissue trauma due to the mechanical stress that the penetration creates.

There is a need to provide an active means of delivering drug into a vessel wall while reducing the mechanical trauma that needles can introduce.

Deflection of the catheter shaft, particularly the distal portions, creates internal strains on components that are necessarily made flexible to enable the catheter to be navigated through tortuous anatomy and directed to various locations within a vessel for delivery of a therapeutic substance. The method used for steerable catheter, as discussed briefly above, involves both a transverse loading and axial loading on components. One consequence of this deformation is a loss in control over an injection needle. For effective treatment, a physician needs to know the exact position of a needle relative to a target tissue. If the needle position relative to the tip of the catheter has changed, due to tension applied by a steering tendon, then it may be difficult to accurately locate the piercing tip of the needle relative to the tissue wall. In view of these shortcomings, there is a need to improve the needle accuracy and repeatability (or NEAR) of a needle injection device, such that the extension of the needle from the tip of the catheter, as a result of an axial translation of the needle at the proximal end of the catheter is accurate and repeatable.

During delivery and use of a steerable agent delivery catheter, the tip of the catheter may experience external forces that can dislodge the tip from the catheter, leading to medical complications. If a tip of a catheter were to become dislodged within a patient, it could potentially enter the patient vasculature, which may lead to severe medical complications. To avoid this occurrence, there is a need for better securement of a catheter tip to the distal end. A typical manufacturing process that bonds a distal tip to the catheter body or stiffening member requires the administration of an adhesive to the parts. Adhesive processes may have variations that are difficult to control and difficult to validate. Therefore, a securement means that is more reliable, i.e., will resist dislodgement of the tip during use, and provides more straight-forward manufacturing process and quality control is needed.

SUMMARY OF THE INVENTION

Whipping

According to one aspect of invention, a catheter shaft design modifies structural properties of the shaft to gain better control over whipping. The modifications include variations in the flexural modulus of the shaft, or portion, that purposely induce whipping over a defined and controllable distance. As a result, torque response of the device is improved since rotation of the catheter becomes more controllable.

In one embodiment, an incremental whipping feature is formed on only a portion of a proximal shaft. The incremental whipping feature may be located proximal the tip of the catheter to produce benefits mostly at the tip, or the whipping feature may be located at shaft sections that will be disposed in conduits areas where maximum bending will occur.

In another embodiment, a catheter includes a section containing one or more maximum and minimum strain energy states as a function of shaft rotation. As the catheter is rotated, the torque response moves between areas of maximum and minimum strain energy to produce a stepwise torque response at the tip. As a result, the tip of the catheter may be more easily controlled when the catheter shaft is rotated. The maximum minimum energy states may be selected to occur at various rotational angles, such as 60 degrees, 120 degrees and 180 degrees rotation of the shaft, which selection can relate to such factors as strength of material, curvature expected, and twist angle. The magnitude of differences between maximum and minimum energy states may be selected according to the torsional and/or flexural properties. The section of the shaft producing the incremental whipping may be modified to increase resistance to kinking or other mechanical problems while still providing maximum and minimum energy states.

The incremental whipping feature aspect of invention may be formed by cut outs or by other methods disclosed herein or made apparent in view of the disclosure.

In another embodiment, a method for locating a tip of a catheter shaft includes placing the shaft tip within a treatment area including locating an incremental whipping section within an area of maximum curvature of the catheter shaft, and rotating the shaft so as to locate the tip at a treatment site. The rotation step may include inputting a predefined torque (or an enforced rotation) at the catheter proximal end to produce a corresponding output deflection that tracks the input. The input rotation may be selected to produce a 180, 120, 90, 72, 60, and 51 degree output.

In another embodiment, a catheter is configured for controlled whipping in rotational increments, wherein a portion of the catheter is forced to assume a curved shape in a patient's vasculature to position a distal portion in an operative position for performing a medical procedure. The catheter includes an elongated tubular shaft having proximal and distal shaft portions, and a lumen therein, the proximal shaft portion configured for transmitting a torque from the proximal shaft portion to the distal shaft portion; a first section of the proximal shaft having a first flexural modulus; and a second section of the proximal end having circumferentially spaced voids, each of which extending lengthwise over the second section. The second section has a flexural modulus substantially higher than the first flexural modulus in the absence of the voids formed in the second section. Thus, if the voids were not formed in the second section the flexural modulus of the second section would be higher than the first section. The second section occupies a position along the proximal shaft portion that substantially assumes the curved shape.

In another embodiment, a catheter's proximal shaft portion includes a first section and second section. The second section is configured to occupy a position along a proximal shaft portion that is forced to assume a curved shape, the second section including a plurality of circumferentially-spaced voids occupying a circumferential section of the second section.

A void includes first and second ends spaced circumferentially from each other, at least one ledge extending into the void, the ledge being disposed between the ends, a gap longitudinally separating the ledge from an opposing surface of the second section, the gap being sized to produce a bending limit for the second section, such that when the second section assumes a first curvature the flexural modulus of the circumferential section of the second section is defined substantially by the summation of the flexural modulus corresponding to each part of the circumferential section extending between voids.

When the second section assumes a second curvature, greater than the first curvature, the ledge abuts the opposing surface so that the flexural modulus of the circumferential section of the second section is approximately equal to the summation of the flexural modulus corresponding to each part of the circumferential section extending between voids and the summation of the flexural modulus corresponding to each ledge of each void of the circumferential section. One example of a second section according to these embodiments is depicted in FIG. 6B of the drawings.

In another embodiment, a catheter includes a distal shaft portion, a proximal shaft portion including a first and second section, the second section being forced to assume a curved shape when the catheter distal portion is in an operative position for treatment of a condition. The second section, configured to incremental whip, may have up to N axes of symmetry where N is the maximum number of axes of symmetry permissible while maintaining a sufficiently large change between low and high energy storage orientations to produce incremental whipping. If the change in energy storage is too low, a release of stored torsional energy of the first section will be too low and exceed the potential energy of the next high energy storage orientation past the next low energy storage orientation, which will cause the shaft to rotate through, rather than increment into that low energy storage orientation.

In another embodiment, a catheter configured for controlled whipping in rotational increments includes an elongated tubular shaft having proximal and distal shaft portions, and a lumen therein, the proximal shaft portion configured for enforcing a rotation at the proximal shaft portion, a control for enforcing the rotation at proximal shaft portion, and means for incrementally whipping a portion of the proximal shaft forced to assume at least some of the curved shape when the torque is applied to the proximal shaft portion.

Needle Extension Accuracy and Repeatability (NEAR)

In another aspect of invention, the needle extension accuracy/repeatability (NEAR) of a needle injection device is improved by locating components relative to a neutral axis (NA) of bending. According to embodiments, the NA may be moved closer to a needle assembly, a tendon assembly may be moved away from the NA or these embodiments may be combined. According to this aspect of the disclosure, a needle's position relative to a marker, or a tip of the catheter may remain unchanged when the distal end is deflected.

According to one embodiment the needle assembly is located relative to the other structural components so that the NA is coincident with the needle axis. Being a zero strain area, therefore, a needle sheath should maintain the same position relative to the needle when a distal portion of the device is deflected. However, in cases where a tendon is used to deflect the distal end of a catheter, the sheath may be compressed relative to the needle due to the tensile load applied to the tendon. In these cases, the needle assembly may be moved to a region that is extended, or in tension when there is a deflection of the catheter tip so that the net change in length is zero.

Alternatively, the NA may be moved by modifying structural components having a high flexural modulus compared with other load bearing structural components. Material may be removed or the structure re-designed so that the NA is re-located to a preferred location.

According to one embodiment, NEAR is optimized to account for deformation associated with both compression of a shaft when a tendon is pulled towards the proximal end, and the bending of a shaft, which (as mentioned above) occurs by virtue of the tendon being located away from the NA. According to one example, a predefined or preferred bending plane is assumed in the device construction. The device is constructed so that the needle assembly lies in a tensile strain area, which counteracts or negates the compressive strain induced by pulling the tendon towards the device's proximal end.

According to one embodiment a stiffener suited for providing axial stiffness for a needle injection device has struts arranged to provide a centrally located NA. The struts may have rounded edges to improve their ability to carry loads in bending, rather than shear.

In another embodiment, an agent delivery catheter configured to improve needle accuracy and repeatability when the catheter assumes a curved shape includes an elongate shaft including a proximal end and a distal end, a tendon disposed within the shaft lumen, affixed to the distal end, and offset from a neutral axis of the distal end to enable deflection of a distal tip by pulling the tendon towards the proximal end; and a needle shaft disposed within the shaft lumen and located approximately coincident with the neutral axis.

In another embodiment, an agent delivery catheter configured to improve needle accuracy and repeatability when the catheter assumes a curved shape includes a deflection spine disposed within the lumen of the shaft at the distal end of the shaft. The spine is configured to increase the axial stiffness of the distal end, has a first and second rib extending parallel and approximately coincident with the neutral axis, and the first and second ribs are fixed to a distal and proximal stabilizer. The needle is disposed within the shaft lumen and is located at the neutral axis.

In another embodiment, an agent delivery catheter configured to improve needle accuracy and repeatability when the catheter assumes a curved shape includes an elongate shaft. The shaft includes a proximal end and a distal end, the shaft being pre-disposed to deflect in a first direction so that a first region of the elongate shaft is placed in tension and second, opposite region is placed in compression. The tendon is disposed within the shaft lumen and affixed to the distal end, the tendon being offset from a neutral axis to enable deflection of the distal tip by pulling the tendon towards the proximal end, whereby the pulling on the tendon compresses the catheter; and a needle is disposed within the shaft lumen, the needle being located in the portion of the first region which offsets the compression induced by the tendon.

According to this embodiment, the arrangement and structure of components within the distal portion of the shaft may have the following characteristics. When viewed in cross-section the neutral axis passes through the center of the cross-section; a pair of stiffening ribs are disposed on opposite sides and lie approximately along the neutral axis; the needle is disposed at a distance from the neutral axis and spaced from the stiffening ribs; and the tendon is disposed at a distance from the neutral axis and spaced from the stiffening ribs and the needle.

In another embodiment, a method for improving the needle accuracy and repeatability for an agent delivery catheter is provided. In this method a catheter is provided. The catheter includes a shaft having a distal and a proximal end, a tendon assembly disposed within the shaft and configured to deflect the distal tip when the tendon is loaded by an operator at the proximal end, whereby the deflected state creates a compressive strain region and a tensile strain region, and the loaded tendon produces a net axial compression on the shaft. The method includes the step of placing a needle assembly in a tensile strain region caused by the deflection such that the elongation caused by the deflection negates the net compression caused by the loaded tendon.

Steering Catheter Tip

In another aspect of invention a needle catheter distal portion includes a tip-spine assembly that provides a secure mechanical engagement to prevent dislodgment when the catheter is being delivered to a treatment site. This aspect of invention is particularly useful for steerable agent delivery catheters that have a relatively weak distal end supported by a stiffener or deflection cage. These catheters use may use a tendon to steer the distal portion. The tip of the catheter, however, is sometimes susceptible to becoming dislodged from the distal portion when the catheter abuts areas of the patient vasculature or guiding catheter. The tip is supported directly by the stiffener but without effecting the flexibility needed at the distal end.

According to one embodiment there is a snap-fit assembly providing a positive interference fit between the tip and spine, exterior jacket or other suitable structure at a distal end of the catheter. In alternative embodiment the engagement may be via a key lock engagement.

The mechanical engagement solves problems with assembly and reliability that are not infrequent occurrences for needle catheters. The solution provided by the invention secures the tip to a stable, relatively stiff element located in an otherwise highly flexible and sensitive area of a needle catheter, i.e., the distal tip, without adversely effecting performance. The prior art, by contrast utilizes an adhesive of bonding, which can fail.

Agent Delivery Without a Needle

Another aspect of invention relates to providing an active means of delivering drug into a vessel wall without relying on a needle penetrating into a vessel wall for delivery of a therapeutic agent. According to this aspect of invention, a pneumatic delivery mechanism is used to propel agent at high speeds into tissue.

This aspect of invention includes devices and methods to facilitate the delivery of therapeutic agents, such as angiogenetic factors, MSCs, anti-proliferative drugs, anti-inflammatory drugs and others, into the myocardial tissue. Current methods of drug delivery into the myocardium wall rely largely on injection into the tissue through a needle that is penetrated into the target region.

According to one embodiment, an agent delivery catheter includes an elongate shaft including a proximal end and a distal end, the proximal end configured for guiding the distal end to a treatment site and the distal end being selectively deflectable by an operator at the proximal end of the catheter; and an agent delivery lumen extending through the shaft from proximal to distal ends and terminating at a distal tip. This tip is configured to expel a pressurized therapeutic agent contained within the delivery lumen. The agent delivery catheter also includes a proximal control including a pneumatic source in fluid communication with a therapeutic agent source, and an actuator for pressurizing the therapeutic agent such that the therapeutic agent accelerates to a velocity sufficient to deliver the therapeutic agent into a target tissue disposed adjacent the tip.

According to this embodiment, the proximal control may include a housing, drive pin and firing mechanism. The housing includes a fluid delivery lumen in fluid communication with a therapeutic agent source, a pneumatic lumen in fluid communication with a pneumatic pressure source, a fluid channel including a proximal end, fluid channel and a distal, tapered end,. The drive pin has a distal end in fluid communication with the fluid channel, and a proximal end in fluid communication with the pneumatic lumen. The firing mechanism is configured to discharge a pressurized gas into the pneumatic lumen.

In another embodiment a method for delivery of a therapeutic agent to a target tissue within a body is provided using a steerable catheter. The catheter has a proximal portion and a distal portion including a tip for delivery of the agent, and a control for injecting agent into a target tissue by way of a fluid delivery lumen extending along a lumen of the shaft and terminating at the tip. The method includes the steps of tracking the catheter to a treatment location, placing the tip adjacent or against a target tissue, introducing therapeutic agent into the delivery lumen until a fluid column occupies the delivery lumen, and activating a pneumatic source using the control such that the fluid in the delivery catheter is propelled out form the tip and embedded in the adjacent target tissue.

Incorporated by Reference

All publications and patent applications mentioned in this specification are herein incorporated by reference to the same extent as if each individual publication or patent application was specifically and individually indicated to be incorporated by reference, and as if each said individual publication or patent application was fully set forth, including any figures, herein.

BRIEF DESCRIPTION OF THE DRAWINGS

FIG. 2 is a side view of the catheter of FIG. 1, not drawn to scale for illustrative purposes. The catheter includes a proximal and distal shaft portion. The distal shaft portion is shown in an un-deformed position. A deflected position for the distal end is shown in phantom. This view also shows examples of control portions for the catheter used to steer or guide the catheter distal end to a target location.

FIG. 3 is a schematic view of the catheter of FIG. 2 with distal end disposed within a ventricle of a patient. The catheter shaft portion adjacent the distal end includes an incremental whipping feature disposed within the aortic valve. The incremental whipping feature provides greater control over the distal end when the catheter is maneuvered into position.

FIG. 5 is a perspective view of a portion of the catheter shaft near and including the distal end. This embodiment of the catheter shaft includes a first embodiment of an incremental whipping feature adjacent the distal end.

FIG. 24 is a close up of the section labeled "FIG. 24" in FIG. 23.

DETAILED DESCRIPTION OF EMBODIMENTS

Figure 1:
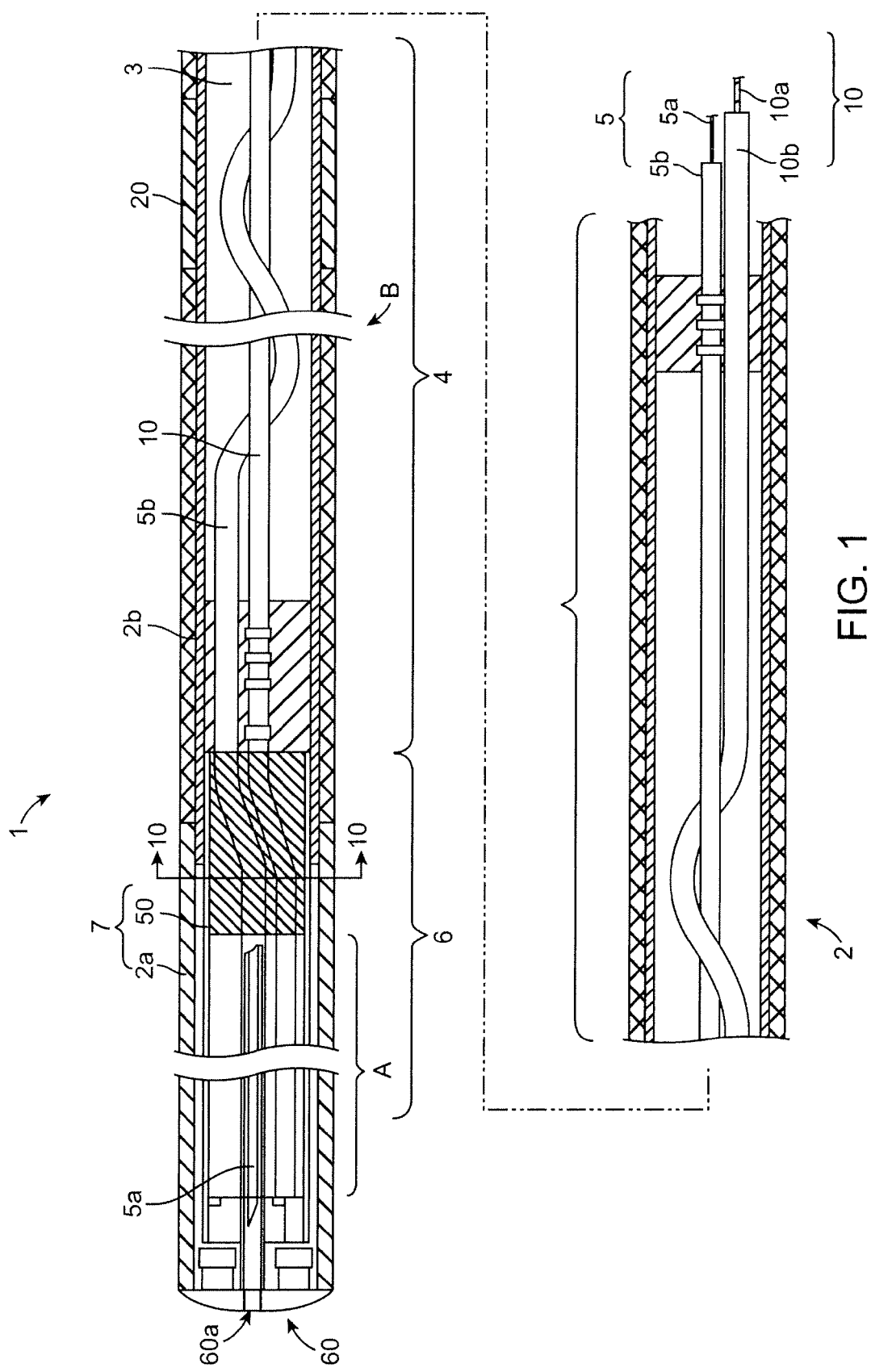
FIG. 1 is side cross-sectional view of a portion of the shaft of a deflectable catheter having a deployable needle at its distal end. The catheter may be used to deliver a therapeutic to a target tissue location located within a body lumen or vessel.

FIG. 1 illustrates a preferred embodiment of a ventricular or atrial deflectable catheter 1 that includes an elongate catheter shaft 2 having a catheter proximal section 4 and a catheter distal section 6. It will be appreciated that the breaks drawn at Section A of the catheter 1 and just distal of section 20 indicate that the actual lengths of those sections are much longer for an actual catheter construction in accordance with the disclosure than is shown in FIG. 1. For instance, as the deflection section A, which extends between the distal material filling the lumen (indicated using cross-hatching in FIG. 1) and the distal stabilizer 56 of the spine 50 is expected to easily deflect using the tendon 10a (as explained below), it should be much longer in length relative to the shaft diameter than is shown in FIG. 1.

The catheter 1 is designed to have a particular torsional, axial and/or flexural stiffness relating to functional purposes of catheter sections and its intended use (or for a general-use catheter), as will be revealed herein. The stiffness properties are intended to optimize performance of the catheter 1. The catheter distal section 6 is more flexible than the catheter proximal section 4. Distal section 6 is flexible so that it may be easily deflected laterally, as depicted in phantom (6-D) in FIG. 2. The catheter 1 may be deflected at distal end 6 by pulling on at least one tendon 10 extending over the proximal and distal sections. A tendon 10a, extending through a tendon sheath 10b is affixed at the distal section 6 and controlled by a steering guide 10c located at the control portion 8 of the catheter 1 (collectively, the tendon 10a, sheath 10b and steering guide 10c will be referred to as a tendon assembly 10). Examples of tendon assemblies capable of deflecting distal section 6, e.g., as shown in FIG. 2, are disclosed in U.S. Publication No. 2005/00780844. According to disclosed embodiments, the deflection, or control of tip 60 using the steering guide 10c is enhanced by moving the tendon connection point at the distal section 6 away from a neutral axis of bending for the distal section 6, as explained in greater detail, below.

Referring to FIG. 2, at the proximal end the catheter has a control portion 8 that includes a shaft 2 steering control 12 and steering guide 10c, a needle control 16 and a connection port 18 for delivering therapeutic agent to a treatment site. Steering control 12 and guide 10c, e.g., those described U.S. Pub. No. 2005/00780844, are used to control the deflection of shaft 2 en route to, and while at the target site by pulling one or more tendons for tip deflection.

A needle 5a is used to deliver therapeutic agents to a treatment site. A sheath 5b extends from proximal to distal ends of the catheter to provide passage for needle 5a to retract and extend from catheter tip 60. Movement of the needle 5a is controlled by a needle control 5c. The needle 5a and sheath 5b will hereafter be referred to as a needle assembly 5. Needle assemblies and control contemplated as embodiments of invention are found in U.S. Publication No. 2005/00780844 and U.S. application Ser. No. 12/022,047. One or more connection ports 18 are used to place an injection needle in fluid communication with a therapeutic agent. Connection port 18 may include a pressure regulator/sensor. In one embodiment of the invention, a needle assembly 5 and control 5c includes a firing mechanism to expel agent at high speeds from the tip 60. The momentum of the expelled agent from the tip 60 is relied upon to penetrate the adjacent target tissue, rather than an embedded end of a sharpened needle. In this case, the control 5c may include a firing mechanism, as will be explained in greater detail below.

As will be appreciated, embodiments of the needle assembly 5 may be practiced by retro-fitting an existing deflection catheter. Accordingly, it should be understood that the needle assembly aspects of invention may be practiced by a needle assembly 5 substituted of an existing catheter. It will be understood that one may retrofit an existing catheter to include other aspects of invention.

In some embodiments, the tendon assembly 10 is located approximately in the center of the catheter shaft and the needle assembly 5 is wrapped around the tendon assembly 10 over at least a portion of the proximal section 4 length, as depicted in FIG. 1. The number of wraps and the location of the wraps may be altered to suit a particular objective, such as to improve the usability of the catheter when it is disposed within a particular type of tortuous anatomy.

The catheter distal section 6 includes a restoring or compression cage 7, which is stiff, axially but with limited or appropriately limited bending stiffness. Compression cage 7 includes a distal section housing 2a portion of the catheter outer shaft 2, and a deflection spine 50. As discussed in further detail, below, the deflection spine 50 may be constructed as one or more elongate ribs connecting a distal and proximal stabilizer. The rib extends over the deflection section A in FIG. 1. The rib should therefore be appropriately flexible in bending to allow the deflection section A to easily deflect when the distal tip is being steered into position.

The distal catheter shaft 2a acts as an outer packaging layer for the internal components of the catheter that are housed in the catheter distal section 6. The compression cage 7 provides columnar (axial) stiffness/strength to the distal section 6 without appreciably increasing its bending stiffness, so that the distal section 6 may be easily deflected via a tendon 10a using the steering guide 10c. The needle assembly 5, which includes needle 5a and sheath 5b, extends parallel to the tendon assembly 10 over the distal section 6 and is disposed at the center of the shaft lumen over distal section 6 in the illustrated embodiment. In other embodiments the needle assembly 5 may be located off-center, as will be explained in greater detail, below. At tip 60 of the catheter there is a passageway 60a formed in the tip 60 for passage of the needle 5a when the tip 60 is disposed at a treatment site.

The proximal portion 2b of the catheter shaft 2 delivers the distal section 2a to a treatment site. One function of the proximal portion 2b of the shaft is to deliver a torque applied via the steering control 12 over the length of the shaft. Flexural and axial stiffness of shaft portion 2b are also important.

Whipping

According to one aspect of the disclosure, the flexural modulus of the catheter shaft proximal portion 2b is modified to assist with directional control of the tip 60 to ensure accurate placement of a treatment agent. The challenges associated with accurate placement of the distal portion 2a can be appreciated by consideration of the example illustrated in FIG. 3. Here, catheter 1 is disposed over the aortic valve and distal portion 6 articulated to place tip 60 adjacent a target tissue, e.g., infarcted tissue, $T_1$ and $T_2$ being located in three-dimensional space along the wall of the ventricle.

In order for tip 60 to be accurately placed at a target tissue site, distal portion 6 is curled using the tendon assembly 10/steering guide 10c. Full, three dimensional displacement of the tip 60 is achieved by a combination of the steering guide 10c and steering control 12, which applies a torque to the catheter shaft 2. Thus, tip 60 may be located in three dimensional space to treat target tissue by a combination of rotation and bending of the distal portion 6.

As will be understood, when a torque T is applied, or, more perhaps more accurately a rotation enforced, via the steering control 12, i.e., an enforced rotation applied to proximal end 4, a wind up occurs in the shaft followed by a transient, dynamic response at the end 6. This transient response is known as whipping. The degree of whipping at distal section 6 depends upon such factors as the orientation of the catheter sections relative to the torque axis, torsional stiffness of the shaft proximal the distal portion 6 and the degree of damping. Whipping can sometimes make it difficult to accurately place tip 60 at treatment sites $T_1$, $T_2$, etc.

According to one aspect of invention, the catheter shaft 2b of the proximal portion 4 is modified to make the catheter 1 more controllable. In particular, embodiments are contemplated where the flexural rigidity, or bending stiffness of shaft 2b is configured to purposely induce whipping, incrementally, over a defined and controllable distance. As a result, torque response at the distal section 6 is improved.

As alluded to above, the physical basis of whipping is the variation with rotational orientation of the flexural modulus or curved moment of the catheter shaft when it is confined in a curved conduit such as the patient's aortic arch or other curved anatomy, or a curved section of a guide catheter. This causes the amount of stored energy in the shaft to vary with rotational angle in a shaft portion that is rotated while it is confined in the curved conduit, thus producing the maximum and minimum energy rotational orientations that result in the whipping. Because unintentionally induced whipping can make it very difficult or impossible to adequately control the distal rotational orientation of the device by rotating the proximal end, a design objective in many conventional percutaneous catheters, especially where rotational orientation is desired, is to minimize whipping. A variety of features and conditions are considered in the design of catheter shafts to minimize whipping. In general, the least whipping and wind-up occurs in shafts with the highest torsion modulus to flexural modulus ratio. Additionally, designing and processing a shaft to have a very uniform flexural modulus or curved moment as it is rotated, while confined in a curved conduit such as the aortic arch, will minimize whipping. Unfortunately, it is not possible, practical or perhaps even desirable to manufacture catheters having perfect symmetry so as to negate whipping, nor is it generally possible or practical to manufacture a catheter shaft having perfect symmetry over its length. As such, a degree of whipping will also be present when a shaft portion is forced to assume a bent shape.

Figure 4A:
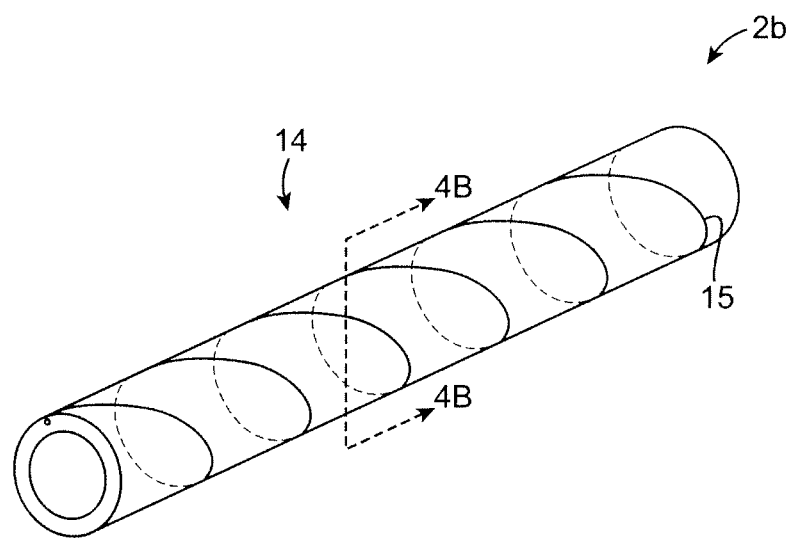
FIGS. 4A-4B show perspective and cross-sectional views of one embodiment of a portion of the proximal portion of a catheter shaft. The shaft includes a single, helically wound wire which increases flexural and torsional stiffness in the shaft.
Figure 4B:
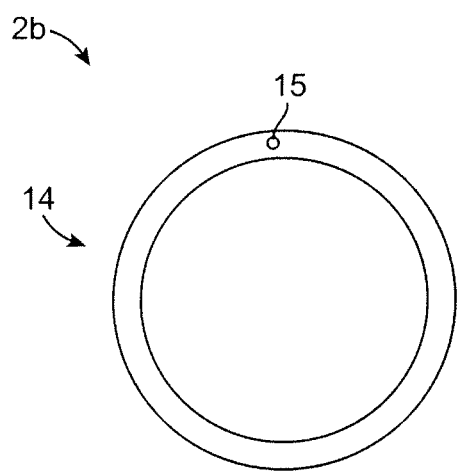

Existing catheter shaft sections for proximal portion 2b are illustrated in FIGS. 4A through 4D. FIGS. 4A and 4B display a shaft 14 with coiled wire 15 construction. In this design, the coiled wire 15 is shown disposed within the wall of the catheter shaft 14. It will be appreciated that the coil may be bonded along the inner or outer surface of the shaft wall with similar effect. The coiled wire supplies increased axial and bending stiffness to the polymer catheter shaft. Also, the torque control is improved since torque will be transmitted along the coiled wire and force the catheter shaft to rotate.

Figure 4C:
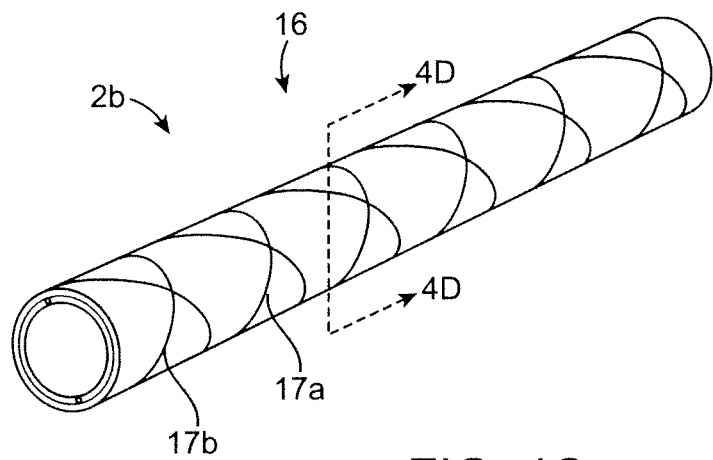
FIGS. 4C-4D show perspective and cross-sectional views of another embodiment of a portion of the proximal portion of a catheter shaft. The shaft includes two helically wound wires which increases flexural and torsional stiffness in the shaft.
Figure 4D:
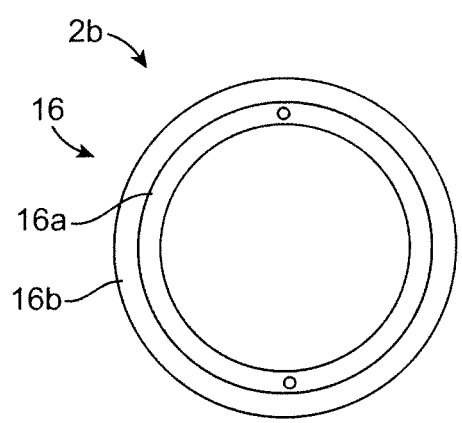

FIGS. 4C and 4D show a catheter shaft section 16 for proximal portion 2b having a simple, two-strand braid 17a, 17b design in which the strands are oppositely clocked and weave to form a stronger overall structure that is more resistant to twist. The cross section (FIG. 4D) indicates that the strands may be disposed between an inner layer 17a and outer layer 17b of the wall of the catheter shaft proximal section 2b. It is also possible to co-extrude the braiding within a single-layered catheter shaft, similar to that shown for the coiled wire example above in FIGS. 4A and 4B. The braid design has improved torque response compared to the single direction coil due mainly to an increase in the torsion modulus to flexural modulus ratio in the catheter confined in the curved conduit. The lower the flexural modulus of the shaft portion in the curved conduit, the lower the unintended changes in flexural modulus with rotational orientation of the bending, thus there are lower changes in shaft stored energy. In the shaft portion proximal (and distal) to the confining curved conduit, the higher the shaft torsion modulus, the less rotation change is required to store or release a given amount of shaft stored energy.

Each of these existing solutions 14 and 16 result in improved torque response of the catheter shaft. Nonetheless, they are susceptible to catheter whipping, which occurs when the catheter shaft stores energy as a first end is rotated, and at some input angle, the catheter releases that energy, causing the output angle to quickly rotate through a relatively large angle until it again matches with the input angle. This phenomenon is well known and continues to be a vexation of catheter design.

Referring again to FIGS. 2-3, as mentioned earlier the proximal section 2b of the catheter shaft is responsible for transmitting much of the torque from the user to the distal end of the device. In a preferred embodiment, a section 20 of distal portion 2b is modified to improve controllability of the tip 60 when the tip 60 is articulated in three dimensional space. Section 20, embodiments of which are described below, may be formed in an existing catheter shaft, or it may correspond to an additional section near the distal end 6. Section 20 may comprise various cut features as described in FIGS. 5-6, which can provide improved torque response. In still other embodiments, the internal components of the catheter, i.e., components disposed within the shaft 2b lumen, may be arranged to improve controllability, or the shaft cross-sectional shape may altered to provide a similar benefit.

FIG. 5 is a partial view of catheter 1 near distal end 6 includes one example of section 20, i.e., circular openings, to control whipping, within or near the proximal section 2b. Section 20 in this case includes rows of holes or openings 21 located at 60 degree increments about the shaft portion 2b. The ability of these rows of circular holes 21 in FIG. 5 to improve torque response at distal end 6 will now be explained.

At the start of rotation, friction on the shaft outer diameter and energy loss due to damping (and overcoming any bend preset in the shaft) requires that a torque/enforced rotation be applied to the proximal end of the shaft before the distal portion of the shaft begins to rotate (in other words, some amount of energy is stored in the shaft and some amount of energy is converted to heat prior to its distal portions beginning to rotate). This twisting rotation required to overcome friction and damping is called "wind-up". Damping can be considered to be friction internal to the shaft. Lowering the friction of the system lowers wind-up. In some cases, the difference between the static friction and the dynamic friction coefficients or changes in friction with a device's rotational orientation can cause changes in wind-up that appear to be whipping. In general, all other properties/conditions being equal, devices with lower friction coefficients, lower flexural modulus, higher torsion modulus or confined in a less curved conduit will have less wind-up. In general, in most percutaneous device designs where rotational orientation control is desired, wind-up is not the major concern, as designs that minimize whipping usually control windup to an acceptable degree before whipping is adequately controlled in the low-friction/blood lubricated vasculature environment.

During rotation induced by an applied torque T (or enforced rotation) at proximal end 4 for the catheter 1 in the position shown in FIG. 3, the amount of stored energy in the shaft 2 increases as the differential in rotational displacement between proximal and distal ends 6, 4 increases, which requires a greater torque to be applied at proximal end 4. When the distal end 6 begins to turn this stored energy is returned to the shaft by increasing the amount of rotation of the distal end 6 relative to the proximal end 4 (causing a decreased torsional resistance to the enforced rotation at the proximal end). When the proximal end 4 is rotated, the distal end 6 will tend to rotate rapidly when approaching, and rotate slowly when leaving rotational orientations where the shaft stores a minimum amount of energy (relative to an adjacent orientation). When the proximal end of the shaft is rotated, the distal end 6 of the shaft 2b will tend to rotate slowly when approaching the rotational orientations where the shaft 2 stores a maximum amount of energy (relative to the adjacent orientations) and then to jump (rapidly rotate) past the orientations with a maximum energy storage (relative to the adjacent orientation).

Thus, when the proximal end 4 of the shaft 2b is rotated, the distal end 6 of the shaft 2b tends to remain at or near orientations with minimum shaft stored energy for longer periods and rotate rapidly past orientations where there is a maximum shaft stored energy. Embodiments of invention alter the flexural modulus of the shaft 2 as a function of rotation angle to provide incremental or controllable whipping behavior as the catheter shaft 2 is rotated to re-position tip 60.

Designing and processing a shaft to have a very uniform flexural modulus or bending moment as it rotates the bending axis, e.g., as catheter 1 in FIG. 3 is rotated about an axis in the plane of FIG. 3, will result in the least whipping. This usually means a uniformly concentric/radially symmetric shaft cross-section design using stress relieved or uniformly stressed materials is required. All other properties/conditions being equal, the least whipping occurs in shafts with the lowest flexural modulus, because the amount of the variation in flexural modulus or bending moment with rotational orientation possible, or as the result of dimensional/material variations is limited/less in lower flexural modulus systems. Thus the stored energy changes with changes in the bending orientation (rotation) of the shaft are lower. Additionally, in general, all other properties/conditions being equal, the higher the flexural modulus, the more applied force to the confining curved conduit and thus, the greater the frictional forces and wind-up.

Another major source of whipping is a preset curve (bend) in the shaft portion confined in the curved conduit. The preset curve is often present as a result of the catheter being packaged in a curved state. When this preset curve and the curve of the conduit are aligned, the shaft has the least bending moment applied to it and thus, is storing the least energy. When the two curves are opposite, the shaft has the most bending moment applied to it and thus, is storing the most energy. Thus, as the shaft is rotated, it is always subjected to changes in stored energy and, thus, has whipping. In general, all other properties/conditions being equal, the straighter the shaft, i.e., no preset curve, or the less tendency to accept a preset bend under use conditions, the less whipping it will have.

Increasing stiffness (torsion modulus) or damping of the shaft system can help to minimize whipping. The higher the torsion modulus of the shaft, the less change in distal rotation for any given amount of stored energy returned to or removed from the shaft and thus, less whipping. Using damping materials in the shaft causes energy to be used up as the distal end of the shaft rotates relative to the proximal end of the shaft, which causes the amount of extra rotation by the distal end of the shaft, during a return of energy situation, to be reduced, as some of that energy is used up in the form of heat (damped). However, this is usually not a significant design avenue, as the more damping, the more difficult (higher torque required) it is to rotate the shaft. All other properties/conditions being equal, the least whipping and wind-up occurs in shafts with the highest torsion modulus to flexural modulus ratio.

The torsion modulus (applied torque per unit of shaft twist) is inversely proportional to the length of the shaft between where the torque is applied and where the torque is resisted. Therefore, all other properties/conditions being equal, the longer the shaft between where the rotation is applied (where torque is applied) and the curved conduit (where the torque is resisted), the more whipping and wind-up. All other properties/conditions being equal, the curvature of distal portions of the shaft due to a confining conduit may cause more whipping and wind-up than the curvature of proximal portions of the shaft due to a confining conduit.

In many shafts or shaft-like constructions or assemblies with a flexural modulus variation with rotational orientation, the variation is relatively regular along at least, a portion of the length of shaft. This is especially true of flexural modulus variations caused by dimensional non-uniformities, lack of cross-sectional radial symmetry, and/or processing induced stresses. Whipping can be minimized in such shafts by causing the shaft and/or the relevant components of the shaft and/or inside the shaft to be twisted/occupy different rotational orientations along the length of the shaft. This works because, while some portions of the shaft confined in the curved conduit are returning energy to the shaft, other portions of the shaft are removing energy from the shaft, and thus the total change in shaft energy storage is reduced. In general, all other properties/conditions being equal, the more twists within the length of the curved conduit, the less whipping.

In a preferred embodiment a catheter torque shaft (proximal section 2b) is modified to produce varying flexural stiffness properties with rotation angle at the section of the catheter shaft 2 disposed within a curved conduit, e.g., the aortic arch in FIG. 3. It is contemplated that by varying between high and low stored energy states with torque response by selectively varying flexural properties in the shaft, as described above, there is provided an incremental whipping effect which may increase the controllability of the tip 60 response to a torque (or enforced rotation) applied at proximal end 4.

Thus, in one embodiment a shaft design configured for incremental whipping control when confined in a curved conduit are features that increase or decrease the flexural modulus of the shaft at the desired rotational incremental intervals. That is, longitudinal shaft portions of a lower flexural modulus are separated rotationally by longitudinal shaft portions with a higher flexural modulus.

In some embodiments, changes in the flexural modulus may be achieved by selectively removing material from the shaft to reduce its flexural modulus, such as depicted in the cut-outs 21 in FIG. 5. The cut-outs can take many forms depending on the intended use. Hence, the section 20 be configured to achieve a particular functional purpose due to its particular form, as will be appreciated in light of the disclosure. Cut-outs or removal of material is preferred because it doesn't result in an increase in the shaft 2 outer diameter (OD) or decrease in shaft 2 inner diameter (ID). In FIG. 5 the lower flexural modulus longitudinal portions are the portions that have a line or rows of holes cut in them and the higher flexural modulus longitudinal portions are the portions of uncut shaft between them. The number of such rows located about the shaft (when viewed in cross-section), or circumferential length of these rows may be varied to increase the number of controlled, incremental rotations (as opposed to, e.g., a single, uncontrolled rotation) or to adjust the rate of rotation, respectively, when whipping occurs.

In some embodiments, only one cut-out is required per longitudinal portion. In one example, a line of cut-outs or equivalent features that decrease the flexural modulus may be rotationally spaced about 120° apart. When this type shaft it is confined in a curved conduit, it will tend to incrementally whip to orientations where the line of cut-outs or equivalent weakened areas align with the inside of the curved conduit. In the case of these features being spaced about 120° apart, there are 3 such rotational increments. If there are only two such lines of holes, cut-outs or weakened areas (causing a decreased flexural modulus) spaced 180° apart, then the shaft will again tend to incrementally whip to orientations where these line of holes align with the inside of the curve. Thus, for a 180° spacing there are 2 rotational increments. Rather than weakening areas along the shaft, the shaft may instead be strengthened. That is, material(s) and/or component(s) may be added to the shaft wall and/or shaft construction in angular increments about the shaft to create higher flexural modulus longitudinal shaft portions separated by "normal" or unaltered lower modulus longitudinal shaft portions. This may, however, not be desired since it can increase shaft OD and/or decrease its ID to an unacceptable amount. Alternatively and more preferred, the material(s) and/or component(s) added to the shaft wall to create higher flexural modulus longitudinal shaft portions may replace or displace a "normal" shaft, material and the increase in shaft OD and/or decrease in shaft ID is minimized or avoided altogether.

In some embodiments, section 20 is constructed to produce a different flexural modulus, either in its construction or material used, so that when material is removed to induce incremental rotation, the (rotational) average flexural modulus of this portion of the shaft is equal to or closer to that of the rest of the adjacent shaft. There are at least two advantages to this type of design. First, the minimum flexural modulus of this portion may raised relative to the other shaft portions so that a bending/curvature in the confining curved conduit is not susceptible to kinking or other types of failure that may occur within the conduit as the shaft 2 is rotated and the weaker section strained. If the minimum flexural modulus of this portion of the shaft is much less than the adjacent portions of the shaft, then the curvature of the adjacent portions of the shaft will tend to be shifted to this minimum flexural modulus portion, possibly causing damaging strains in this portion of the catheter or unacceptable weakening (e.g., increasing the possibility that a kink will occur, lowering the torsion modulus, failure in torsion and/or lowering the axial strength in compression or tension, or damaging internal components of the catheter). Second, in some embodiments the differences in minimum and maximum strain or stored energy (or maximum or minimum flexural modulus) may be maintained or even increased while avoiding a very weakened shaft portion. For instance, a section of a braided shaft could have its jacket replaced with a plastic, or plastic blend shaft section 16, 17 described above with respect to FIG. 4, which provides a higher modulus jacket during shaft construction. Such a jacket could have sections, spaced about the circumference, formed by a higher or lower modulus than adjacent sections.

Such a jacket could also be formulated to have a different color to allow its identification in later catheter processes to ensure that its position at a shaft longitudinal position is suited for the particular conduit where the proximal shaft portion will be relative to the tip 60, e.g., section 20 located within aortic arch in FIG. 3. Further, the color identification may be useful to identify where the incremental rotation inducing features may be cut or produced for the given location. Furthermore, such a jacket could also be formulated to have a distinctive appearance under appropriate medical imaging technologies, such that section 20 may be confirmed to be appropriately confined in the desired conduit (forced into a curved condition).

Figure 6A:
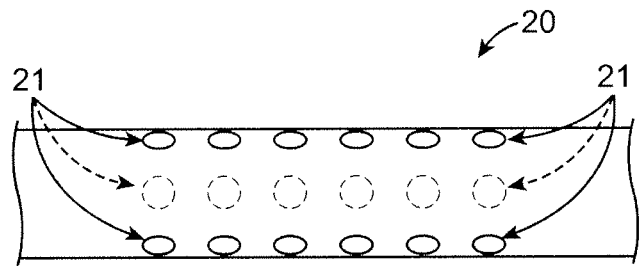
FIGS. 6A-6B show second and third embodiments of an incremental whipping feature for the adjacent portion of the catheter shaft of FIG. 5.

Various embodiments of section 20 are illustrated in FIGS. 6-8. FIG. 6A illustrates the embodiment shown in perspective view in FIG. 5, but with the rows of holes located 120 degrees apart from each other. In the example illustrated in FIG. 5, the incremental whipping feature may produce an incremental or stepwise change in the whipping rate for each 60 degrees of rotation. That is, the rate at which section 20 rotates (hence the distal portion 4 as well) will increase/decrease for every 60 degrees of rotation when the bending stiffness associated with the curvature moves between maximum/minimum energy states. In the embodiment of FIG. 6A this change in state occurs for every 120 degrees of rotation.

Figure 6B:
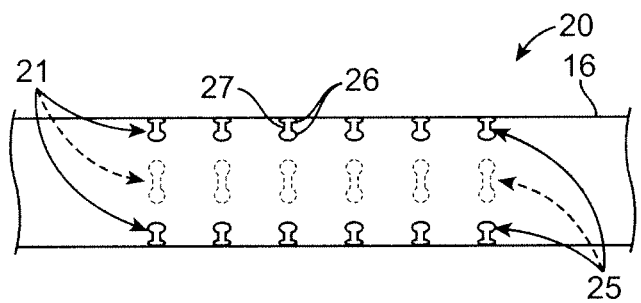

In FIG. 6B there is an embodiment where cutouts 25 are shaped to produce a variable flexural rigidity. Each of the rows are spaced 120 degrees apart in this example. Thus, a circumferential section contains three such cutouts. A cutout may be made to create a formed hole 26 at each end, e.g., a substantially circular hole, and two opposing ledges disposed between holes 26 and defining a gap 27. These surfaces formed by the cutout are used to achieve a reduced flexural modulus over a limited bending angle. When this bending angle is reached, the ledge surfaces come together to interfere with each other, thereby increasing the effective flexural modulus by abutment of the surfaces.

A void may be formed to create a variable stiffness property. A void may include a through hole, e.g., FIG. 6B, or material excavated, removed, absent from or only partially through, a groove, slit or slot. One or two ledges may be formed, e.g., a ledge may oppose a surface that does not extend into the void. A void may have a regular or irregular shape having a ratio of circumferential-to-longitudinal extent greater than 1, e.g., the cutout of FIG. 6B. As explained earlier, the appropriate manner in which a section should be modified depends on the intended use, e.g., the control needed over the working element of the catheter, and the material properties of the catheter shaft section after modification, such as its elastic range, resistance to kinking, need to protect internal components, etc.

In these embodiments the shaft design can prevent excessive shaft curvature while still maintaining a lower stored energy to produce incremental whipping within a predetermined bending range. A higher ratio of low energy to high energy storage also becomes possible because a lower modulus is limited to a defined bending range. This approach for incremental whipping may be especially useful for the section 20 metallic tubes, which can have greater susceptibility to kinking. The width of the gap may depend upon the flexural rigidity of the circumferential section before the surfaces abut, which may depend on the degree of which the section can safely accept strain without causing failure. Additional factors include the desired ratio of strain energy storage states over the section, or number of minimum storage states, as alluded to above.

In other embodiments, a stent-like structure may be adopted for section 20. In these embodiments longitudinal portions having a lower flexural modulus are rotationally separated by longitudinal portions having a higher flexural modulus are positioned/held in the ID or on the OD of the shaft, or incorporated into the shaft wall to create an incremental whipping feature.

In another embodiment, shaft/device components within the lumen of shaft 2 that provide a degree of flexural rigidity to the shaft 2 are arranged to produce longitudinal portions of a lower flexural modulus rotationally separated by longitudinal portions with a higher flexural modulus. An incremental whipping feature for a section 20 may also be produced in this manner.

Figure 7A:
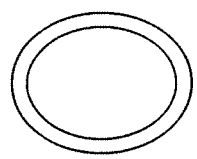
FIGS. 7A-7C show cross-sectional views of a catheter shaft having a 180 degree incremental whipping feature.
Figure 7B:
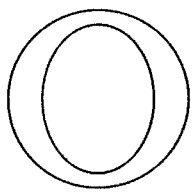
Figure 7C:
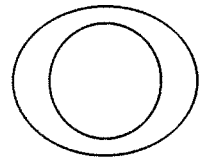
Figure 8A:
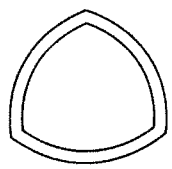
FIGS. 8A-8C show cross-sectional views of a catheter shaft having a 120 degree incremental whipping feature.
Figure 8B:
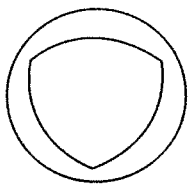
Figure 8C:
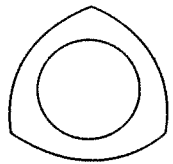

FIGS. 7A-7C and FIGS. 8A-8C are examples of shaped tubes that may produce an incremental whipping feature for every 120 or 180 degrees of rotation. FIGS. 7A-7C illustrate tube cross sections that produce maximum/minimum energy states every 180 degrees. These embodiments show a circular ID and oval OD, oval ID and oval OD, and circular OD and oval ID. FIGS. 8A-8C illustrate tube cross sections that produce maximum/minimum energy states every 120 degrees. The shapes for ID and OD for each embodiment are self explanatory. Two or more of the embodiments in FIGS. 5-8 may be combined.

An incremental whipping section 20 may also be described in terms of cross-sectional axes of symmetry of the flexural modulus. For example, the embodiment shown in FIG. 8A has three axes of symmetry, whereas the body shown in FIG. 7A has two orthogonal axes of symmetry. Further, the embodiment depicted in FIG. 6A, when viewed in cross-section, has three axes of symmetry when three equidistant strips of voids 21 are used, but has two axes of symmetry when only two equidistant strips are used. A circular tube, by contrast, as an infinite number of axes of symmetry, or a polar axis of symmetry. Thus, for example, an applied bending moment about an axis of symmetry for the tube of FIG. 7B will produce a deflection substantially limited to the bending plane. A moment applied, e.g., at 45 degrees from this axis, will, however, produce a deflection outside of the bending plane. In other embodiments, the number of axes of symmetry may be greater than three. It is contemplated that, for many catheters in use today, the number of axes of symmetry may range from between two and twenty.

Stated in perhaps more general terms, an "axis of symmetry" of a body, in connection with the description of section 20 according to the disclosure, refers to the symmetry (or lack thereof about a bending axis of the flexural modulus of material having a predominant effect on the stress/strain distribution equilibrating an externally applied load. A body that has an axis of symmetry, or lacks symmetry for a particular axis of bending, for purposes of this disclosure, means that the body is intentionally assembled, formed or manufactured in such a way that there results a lack of symmetry, or substantial symmetry for bending axes. The meaning of lack of symmetry does not encompass non-symmetries that result from imperfections in a manufacturing or assembly process.

In some embodiments, where the orientation of the curve of the confining conduit relative to the anatomy is known or is within suitable limits, the orientation of the incremental rotation inducing features may be controlled relative to the work element to help assure that the work element may be incrementally whipped toward a desired anatomical feature or direction or does not direct the work element toward an undesired anatomical feature or direction. For example, in the case of FIG. 3 section 20 may be constructed so that when the catheter 1 is in the position shown, the tip 60 is not whipped at a high rate away from a treatment site in the ventricle.

In theory, one could design to have any number of rotational increments, but there are practical limitations. For instance, as the number of angular increments is increased for section 20, the maximum possible difference between the minimum and maximum flexural moduli (difference in minimum and maximum stored energy) is decreased. Thus, in practical systems, one reaches a point where the designed differences between the minimum and maximum flexural moduli (change in shaft energy storage) is near to or less than the differences due to unintended whipping sources and/or changes in stored energy in other portions of the shaft and thus, incremental control of the rotation will be lost. Also, the lower the differences in minimum and maximum stored energy/the lower the energy gradient between the rotational orientations of minimum and maximum stored energy, the lower the forces tending to keep the shaft at the minimum energy storage rotational orientation. Thus, all other conditions/properties being equal, the more designed rotational increments, the less accurate/repeatable the increment of rotation can become. Also, as the number of rotational increments is increased, the change in applied torque during rotation is also decreased since the section 20 will have less change in stored energy. Thus, at some point a change in applied torque can no longer be reliably detected by the user or machine applying the rotation and thus, while incremental rotation may still be occurring it can't be reliably controlled. In some embodiments, the wind-up, conduit curvature and other system properties are known or within limits. For these embodiments, it is possible to control the rate of incremental rotation by controlling the amount of rotation applied to the proximal end of the shaft without detecting a change in the applied torque.

While it is not necessary to equally space rotationally repeating elements, such as illustrated in the drawings, it is preferred in order to create equal rotational increments that equalize the forces that tend to retain a rotational orientation increment at or near the desired change in rotational orientation and thus, have comparable accuracy in each rotational increment. This also provides the maximum minimum torque change per increment (allows the largest number of detectable increments) and regularizes the amount of rotation the user must apply to effect an incremental change in rotational orientation (ease of use).

It is preferred that an incremental whipping section exhibit about the same maximum and minimum flexural modulus/ energy storage/rate properties at each increment. In some cases, where these properties are quite different and the arc of the lower flexural modulus longitudinal shaft portion is too low, it is possible for a shaft to have enough stored energy to rotate through at least one of the next maximum energy storage orientations, thereby producing a larger than desired rotation at the distal portion 6. The next energy storage peak is sufficiently lower than the energy storage peak just passed. The shaft encounters the next high energy storage state before it has rotated sufficiently to shed enough strain energy to remain confined in the next low energy state; that is, it increments past the next low energy state.

The longer the longitudinal length of the incremental rotation inducing features, i.e., section 20, within the curved conduit, the greater the possible change in shaft energy storage during rotation and thus, the more detectable and controllable the increments may be. However, consideration must be given to the length of the confining curved conduit where the tip 60 (or working element, generally) is or will be disposed and the longitudinal positions (device advancement and withdrawal) desired for the device, so that the incremental rotation inducing features sufficiently reside in the confining conduit. If portions reside in a different curved conduit having a different orientation or curvature, this will cause undesired/ anticipated changes in orientation of the tip 60, or applied torque during device use.

In a preferred embodiment of the ventricular or atrial catheter of FIG. 1, the confining conduit is the aortic arch and a substantial portion of the catheter distal of section 20 is disposed within ventricle (FIG. 3) or other non-curved anatomy.

Thus, a significant portion of the catheter distal of section 20 is not confined in a curved conduit and therefore, regardless of its design or shape (within practical limits), will not contribute to the whipping of the catheter/not interfere with the incremental whipping induced by section 20. If the distal portion, about 15-20 cm proximal of tip 60 (or larger in some diseased states), is well designed with an adequate torsion modulus, then the section of the catheter distal to section 20 will adequately follow the rotation of section 20 (i.e. the tip 60 will adequately follow the incremental rotation).

Additionally, consideration must be given to the applied torque and torsion modulus with respect to the selected rate or increments for incremental whipping, as the maximum twist of section 20 over its length may vary considerably from the desired incremental whipping. Thus, when the twist angle approaches the designed increment, e.g., 60 degrees, 120 degrees, the change in stored shaft energy with rotation reaches a minimum and the ability of section 20 to cause incremental whipping is reduced. This effect is much the same as the method of minimizing whipping by twisting the shaft or shaft elements responsible for the whipping, as discussed earlier.

Other methods to produce incremental whipping for a shaft confined in a curved conduit involve manipulation of the shaft's material properties. Such manipulations may produce longitudinal shaft portions of the shaft material that exhibit different stress-strain curves and thus, store energy differently. Such changes could be the result of heating and cooling temperatures and/or rates differentially applied to the shaft via such devices as lasers, quenching fluids and/or heat sink, shielding or other fixtures. For instance, in 300 series stainless steel (SST) hypotubes (a shaft-like construction) the tensile yield of the SST may be designed to be a high value due to the drawing schedule (work hardening) of the hypotube. Raising the temperature of longitudinal shaft portions to the annealing temperature of the SST can produce orientations that at the "in use" curvature are subjected to strains in excess of their yield values and, thus store less energy at that curvature than rotationally adjacent longitudinal shaft portions that did not reach the annealing temperature. In another example, superelastic material shafts may be temperature manipulated in a similar manner to produce longitudinal shaft portions with different loading and unloading stresses, such that the shaft's energy storage changes with rotational orientation at the "in use" curvature. In another example, a highly longitudinally orientated polymer shaft (for example, due to the extrusion process and/or longitudinal stretching) may exhibit a relatively high modulus/high yield stress in bending and the application of an elevated temperature to longitudinal shaft portions may reduce or destroy the orientation of the polymer chains in those portions, lowering the polymer's modulus/yield stress. Thus, during "in use" bending, the energy storage characteristics of the shaft will change with shaft rotational orientation. Such methods as these may be less preferred due to the time, equipment and expense required to control the temperature and temperature differences of longitudinal lengths of the shaft at different shaft orientations over the period of time necessary to effect a material property change. Such manipulations may become particularly challenging in small metallic shafts that are solid or have thick walls.

In other embodiments polymers may be cross-linked using radiation or by chemical means to produce longitudinal portions with different stress-strain curves than adjacent longitudinal portions that are not crosslinked. In other embodiments shaft material properties are degraded (stress-strain curve change) by changing the material's molecular composition using such mechanisms as UV degradation, oxidation, chemical etching and the like. These embodiments may not be preferred as the degraded material can adversely affect such that properties such as biocompatibility, particle generation, shelf life and the like.

As mentioned earlier, section 20 may be disposed in a portion of catheter shaft 2 comprising a construction substantially similar to the remainder of the proximal outer shaft, or not. For example, since the proximal outer shaft 2b includes an inner braid construction (FIG. 4) to improve support, it may be somewhat more difficult to dispose cut-out features therein without damaging or being obstructed by the braiding. Thus, an additional catheter section may be preferable. The additional catheter construction may have a single-walled or composite tubular construction that can be more easily modified with, e.g., cut-out features such as those illustrated in FIGS. 5-6.

The section 20 may be positioned only in a portion of the proximal shaft section 4 that is forced to assume the curved shape of the aortic arch, as depicted in FIG. 3. Or section 20 may be primarily disposed here. In FIG. 3 catheter 1 exhibits the greatest amount of bending within the aortic arch and through the aortic valve during operation. Portions proximal and distal to these zones are not in significant bending and will not see significant benefit from an incremental whipping section. This is because energy is not stored to the same degree in a straightened section and therefore whipping is not an issue. Since formation of, e.g., a cut feature, does not add value to portions of the catheter that are relatively straight during operation, cut features may be omitted from these portions to maximize manufacturing efficiency and economy.

One major advantage of the invention over previous attempts to address whipping is that by implementing, e.g., a cut-out feature, only in the bent portions, substantial torque response benefits may be achieved with comparatively smaller costs compared to forming a device with incremental whipping features over the entire proximal outer shaft portion 2b. Also with respect to manufacturability, section 20 may be formed in the torque shaft or another shaft component using well known fabrication processes. For example, cut features may be formed by laser cutting, micro-machining, photolithography, and in the case of metallic catheter components, EDM. Other processes may be used by one skilled in the art to form cut features within a catheter shaft in accordance with this invention.

In another alternative embodiment, the catheter shaft may be constructed so that section 20 occupies only the portion of the catheter shaft 2 that will reside within the aortic arch (FIG. 3), while the remainder of the shaft 2 may be constructed of a relatively cheap braided shaft. As a result, the cheaper braided shaft design (FIG. 4) may be used for the long proximal portion of the shaft where the torsion modulus is high and there is little fluctuation in shaft stored energy in order to maintain a relatively low cost of manufacturing and a higher benefit-to-cost ratio. Similarly, if an additional section of different curvature exists in other anatomy, e.g., a vein, artery, or in an guiding catheter, this other area of curvature may be chosen for the location of section 20 in accordance with the disclosure.

Figure 9A:
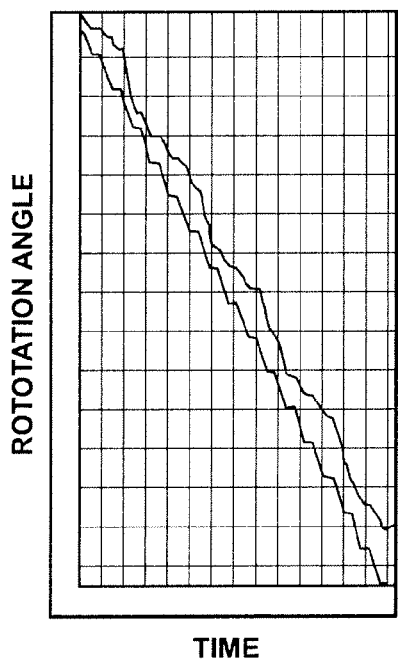
FIGS. 9A-9B are plots showing input and output rotations at a proximal end and distal end, respectively, for a catheter with its proximal section formed from a hypotube and having a high degree of torsional stiffness. The plots show a change in rotation angle verses time. The plots are intended to demonstrate a near idealized stepwise change in output rotational angle at a distal end of a shaft (as regards a desire to minimize whipping) for each enforced rotation at the proximal end.
Figure 9B:
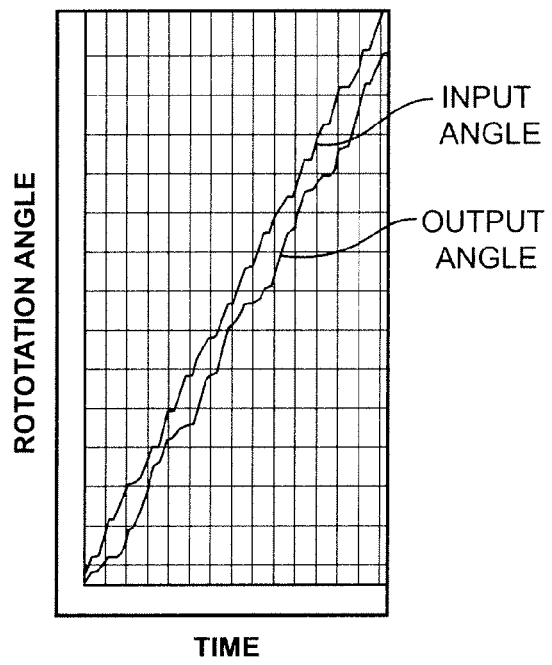

The effect of a design incorporating incremental whipping feature will now be explained further with reference to FIGS. 9A-9C. FIGS. 9A-9B depict the input and output rotations verses time for a catheter shaft having a minimal amount of whipping. It is a deflection catheter in accordance with FIG. 1, but with a proximal shaft, formed from a laser-cut hypotube and not a braid, having a high degree of torsional rigidity and with its distal end confined in a curved conduit similar to FIG. 3. This distal end was naturally straight and testing was per-formed immediately after the catheter was inserted into the curved conduit. FIG. 9A shows the input clockwise rotation at the proximal end (lower curve) and clockwise output rotation at the distal end (upper curve). FIG. 9B shows the input/output rotation for a counterclockwise rotation. In the absence of any whipping, these two curves would have an identical slope. The observed result is a very good following of the output angle changes with the input angle changes during enforced proximal rotation, but with small rotational jumps related to the whipping caused by the unavoidable non-uniformities of the distal portion of the catheter that is confined in the curved conduit (forced to assume a curved shape). Such a shaft is, however, not practical for use because of its high bending stiffness, fatigue failure properties when rotated within tortuous anatomy and high cost, as well as other reasons as will be subsequently discussed. However, such curves represent the best response that may be approached with incremental whipping designs.

Figure 9C:
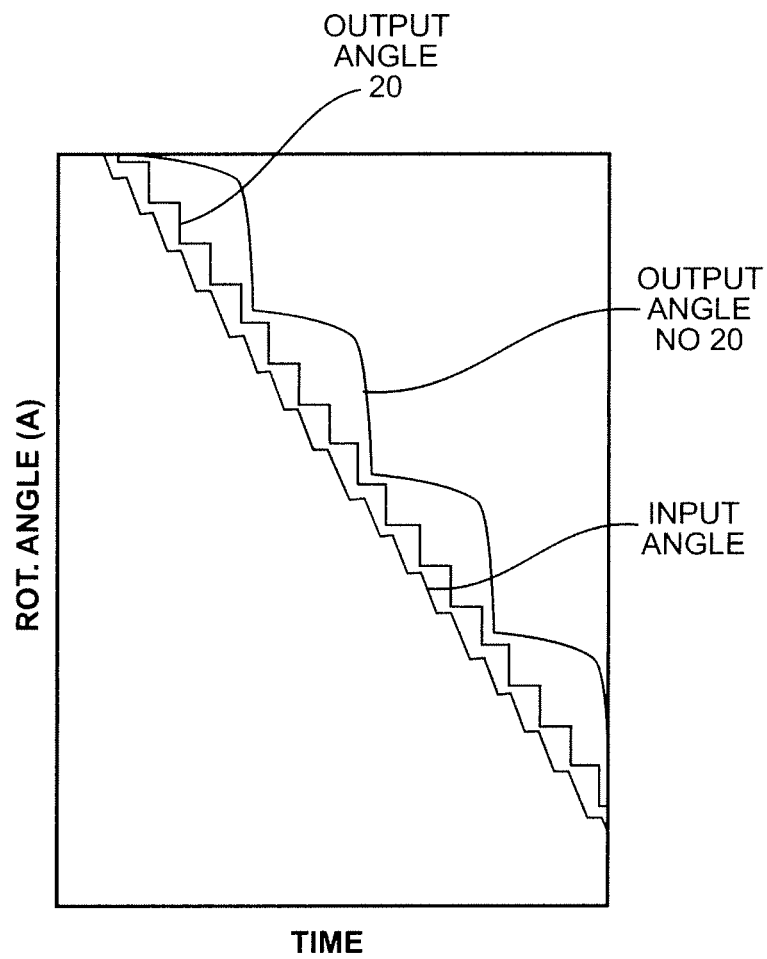
FIG. 9C is a plot showing the output rotation angles for each of two shaft types verses time, in response to an enforced rotation at the shaft's proximal ends. The first shaft is braided shaft that does not incorporate an incremental whipping feature according to the disclosure. The rotation response at the distal end occurs after approximately every 360° degrees of rotation at the proximal end. A high degree of whipping. The second shaft has low energy storage orientations for approximately every 90° degrees of rotation. The stepwise output rotations more closely follow the input rotation (angle) and therefore, are more controllable.

FIG. 9C illustrates a clockwise input/output rotation for a similar catheter with a braided shaft that is, relative to the hypotube of FIGS. 9A-9B, more flexible and with a lower torsion modulus, and the same catheter having an incremental whipping section formed in the proximal shaft section which is forced to assume a curved shape in the confining conduit. The catheter having no incremental whipping section whips for every 360 degrees of input rotation, which is undesired as it is difficult to control. This type of whipping is typical of catheters that have a preset bend in the portion of the catheter confined in the curved conduit. Such a present bend may be created by the packaging of the catheter or more commonly produced by the confining curved conduit due to the viscoelastic nature of plastic and the practically unavoidable time it is left in a curved state during the medical procedure. The same catheter having the incremental whipping section 20, in this case a section 20 having a low energy storage orientation for every 90 degrees, increments for every 90 degrees of input rotation. This type of shaft is therefore easier to control.

With regards to the braided shaft example having an incremental whipping section 20 in FIG. 9C, if the number of low energy storage orientations is increased to say, 5, 6, 7, etc. then the number of incremental whipping steps may be correspondingly increased to 5, 6, 7, respectively, which can increase operator control over the catheter as the proximal end is rotated to reposition the working element. Thus, as the number of low energy storage orientations increases, the output rotation of FIG. 9C may begin to resemble the output rotation exhibited by the hypotube in FIG. 9A. However, as alluded to earlier, there are practical limits to the number of low energy storage orientations that may be made. In general, a section 20 design best suited to address the whipping problem, i.e., one that best controls whipping, for a section forced to assume a bent shape while in a curved conduit should appropriately balance the desire to have more axes of symmetry (so that the rotation response best matches the shaft of FIG. 9A) while maintaining a change in energy storage sufficient to prevent the shaft from rotating through a low energy storage orientation. Larger diameter catheters, for example, should be better adapted able to have an increased number of low energy storage orientations than smaller diameter catheter shafts.

Needle Extension Accuracy/Repeatability

According to another aspect of the disclosure catheter components within the shaft are located relative to each other to improve the accuracy and repeatability of needle deployment, regardless of the curved shape the catheter shaft. Referring to FIG. 1, it is desirable to be able to know exactly the location of the terminal end of the needle 5a relative to the tip 60 of the distal portion 6. When the catheter is straight, the relative locations are known by design. However, when the catheter is bent, the elongation and/or compression of the needle sheath 5b relative to the needle 5a, resulting from the bent condition, will displace these components relative to each other because the needle is far more stiffer than the sheath. Thus, when the catheter 1 is bent as in FIG. 2 and 3, the relative position of the tip of the needle 5a to the terminal end of the sheath 5b and/or tip 60 changes. This introduces possible inaccuracies making it difficult for a physician to accurately embed the needle at the target site.

Deflection of the distal end 6 of the device is primarily enabled through two components: the tendon 10a and restoring or compression cage 7. The tendon 10a, when pulled, puts a compressive force on the distal end 6 of the catheter 1 in a direction slightly off of the catheter neutral axis, causing the tip 60 to deflect and the distal end 6 of the catheter to curve (as illustrated in phantom in FIG. 2). When this tension is released, the restoring cage 7 exerts a restorative force that tends to straighten the distal end 6 toward the original orientation. The restoring cage 7 comprises both a deflection housing 2a and a deflect spine 50, which may also be referred to as the stabilizer components, since it prevents catheter kinking, in addition to restoring the original shape of the catheter 1 after deflection.

In the undeflected state, the neutral axis (or NA) of the catheter 1 coincides with the flexural centroid of the catheter cross-section. The NA is the location in the bending plain having zero-strain during curvature. Load bearing structure on one side of the NA will be in a compressive or tensile strain state, while load bearing structure on the opposite side of the NA will have the opposite strain state in order to maintain equilibrium. The neutral axis may change slightly during catheter deflection, as strains are introduced into the catheter body by the deflection forces initiated by the tendon 10a. However, any structure coincident or close to the NA will, by definition, not deform axially. Since structure at the neutral axis distance maintains a constant length, if it were possible to place the neutral axis along the needle axis, then the accuracy of needle 5a deployment and repeatability (NEAR) for different curvatures of the shaft 2 would be improved, since the needle 5a length in relation to the catheter distal end 6 or tip 60 length would remain constant.

Figure 10:
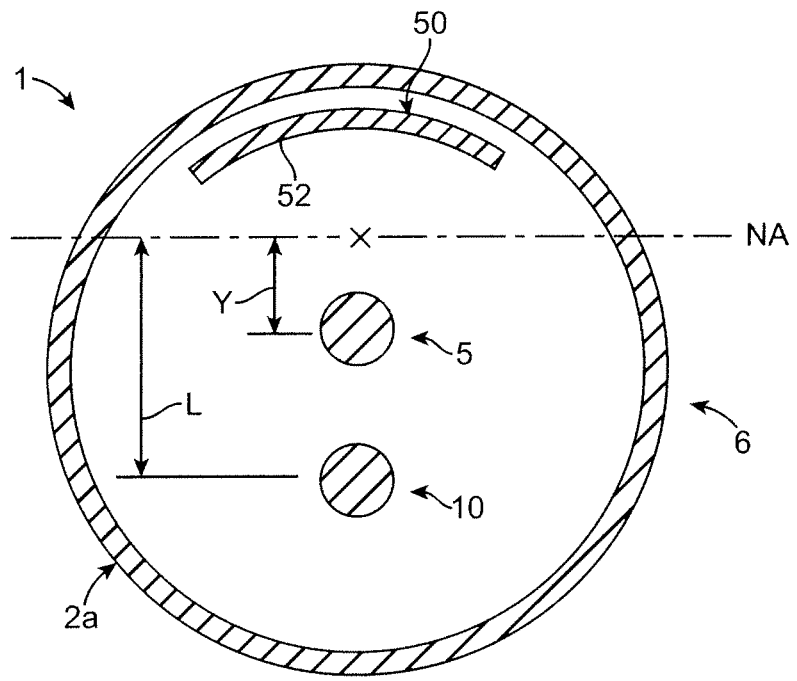
FIG. 10 is a cross-sectional view of the distal end of the catheter shaft taken at section 10-10 in FIG. 1. Also shown is a neutral axis for the cross-section.

FIG. 10 shows a cross-sectional view of the distal portion 6 of the catheter 1 taken at section line 10-10 in FIG. 1. The distal jacket 2a houses the deflection spine 50 near the perimeter of the jacket 2a. The needle assembly 5 (sheath 5b and needle 5a) and tendon assembly 10 (tendon 10a and sheath 10b) are positioned below the deflection spine 50. The NA lies near the deflection spine 50 since this structure has the highest flexural modulus of this cross-section. The needle assembly 5 is offset from the NA by a distance Y from the neutral axis while the tendon assembly 10 is offset by a greater distance L from the NA.

When the catheter 1 is deflected, structure not coincide with NA in FIG. 10 will be subjected to compressive or tensile strain. Thus, when distal portion 6 is deflected by pulling on the tendon 10a, portions below the NA in FIG. 10 will be placed in compression (excluding the tendon 10a, which remains in tension). The compressive strains will result in shortening of the needle sheath 5b. The needle 5a, which is not coupled to the sheath or other structure, will freely move within the sheath 5b when the tip deflects. Thus, as the tip deflects the distance between the needle tip and the end of the needle sheath (as well as the distance between the needle tip and the device tip) changes. This change in position correspondingly alters the relative position of the needle 5a tip and the tip of the catheter relied on by an operator to accurately extend the needle a preset distance into a target tissue during a procedure. This variation in relative position caused by the deflection contributes to non-optimized NEAR.

Figure 11:
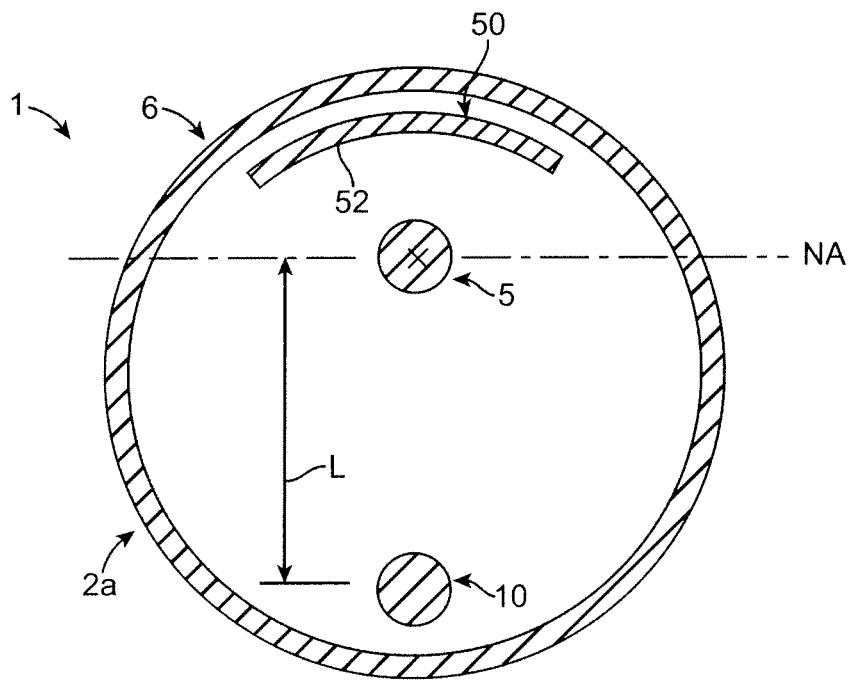
FIG. 11 is a cross-sectional view of the distal end of a first embodiment of a catheter shaft configured to optimize the Needle Extension Accuracy and Repeatability (NEAR) for the catheter. In this embodiment, the needle for the catheter lies coincident or close to the neutral axis of the cross-section.

FIG. 11 is an alternative embodiment. As depicted, the needle assembly 5 has been moved toward the spine 50 so that it lies on the NA. Additionally, the tendon 10a has been moved towards the outer jacket 2a and away from the NA. As such, when the catheter 1 is deflected, the needle 5a/needle sheath 5b, now coincident with the NA, will exhibit little change in relative length. This should improve NEAR. Moreover, by moving the tendon 10a away from the neutral axis increases the applied bending moment since the moment arm L is increased. This can make catheter deflection and control easier to achieve and more ergonomically comfortable. Moreover, by increasing the moment arm, thereby reducing the amount of applied force needed to deflect the tip, the proximal shaft will compress less axially. By reducing the amount of compression, the relative movement of the needle 5a relative to the tip decreases. In a preferred embodiment, the needle is actually placed in the tensile strain region (adjacent the rib 52 in FIG. 11) in order to compensate for the change in length caused by compression of the tip, as described in greater detail, below.

Figure 12:
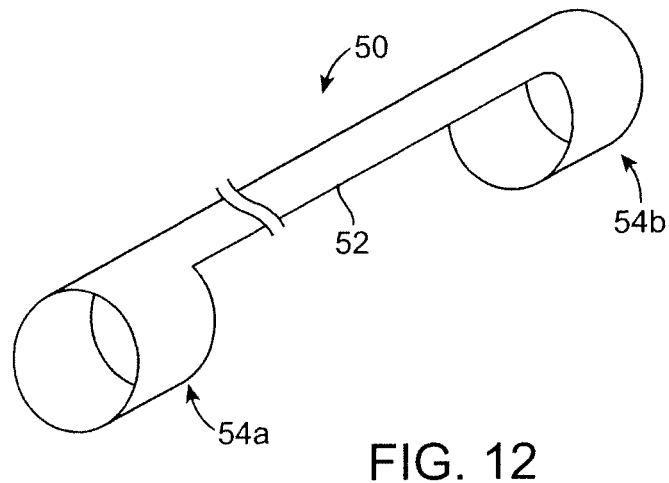
FIG. 12 is a perspective view of a deflection spine of the catheter of FIG. 1. The deflection spine is part of a restoring or compression cage portion of the distal end of the catheter of FIG. 1.

FIG. 12 illustrates a perspective view of the deflection spine 50. Functionally, this component is relied on to add axial stiffness to the distal portion 6. The spine 50 may include an elongate member, stiffener, rib or strut 52 and semi-circular (or circular) stabilizers 54a and 54b. As will be appreciated, the NA illustrated in FIG. 12 will move away from the strut 52 and towards the center of the cross-section if the flexural modulus of the stiffener is reduced, or the location of the stiffener 52 is changed.

Figure 13:
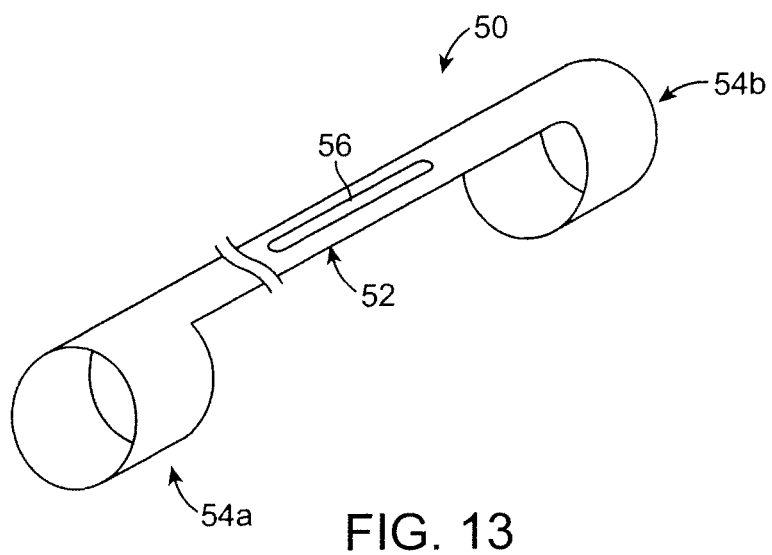
FIG. 13 is a second embodiment of the spine of FIG. 12 showing material removed from a stiffening rib of the spine.

In alternative embodiments of catheter 1 the stiffener may have material removed to improve NEAR. FIG. 13 shows one possibility. A slot is formed in the stiffener 52 so that its flexural modulus for the cross-section of FIG. 10 is reduced. By reducing the stiffener 25 percentage contribution to the overall flexural modulus of the cross section of FIG. 10 the NA should move away from the strut 52. Hence, the moment arm Y is reduced, resulting in less relative movement between the needle 5a and sheath 5b and NEAR improves. In other embodiments the stiffener may be tapered or the strut 52 moved to another location for purposes of changing the position of the NA. Alternatively, a series of holes may be drilled in the spine 50. In still other alternative embodiments, the spine 50 may be thinned to reduce its flexural modulus, such as at the stabilizers 54a, 54b. It will be understood that the effective NA may also be moved by making the spine 50 more flexible or compliant at the stabilizers 54, since the actual strain elongation or compression of the needle 5a or sheath 5b is determined from the integral over the length of the distal portion 6.

In some embodiments the design of the stiffener may take into consideration the bending axis intended for the catheter. For instance, if the catheter distal end 6 will predominantly deflect about only the horizontal axis depicted in FIGS. 10-11, a stiffening member (either strut 52 or additional struts, in the case where material is removed from stiffener 52) may be located along the bending axis, at the opposing side of the sheath 2a, or along the midpoint. For these embodiments the NA may be moved away from the strut 52 located far from the bending axis because there is a higher percentage of load-bearing material, or flexural modulus (a greater percentage of the compressive/tensile strain induced by the deflected distal portion 6 is carried by structure other than the strut 52).

In some cases, the NA is preferably shifted nearer to the needle 5a to improve NEAR. In other embodiments it may be desirable to move the needle 5 away from the NA and into an area that is experiencing an extension when the tip is deflected.

Figure 14:
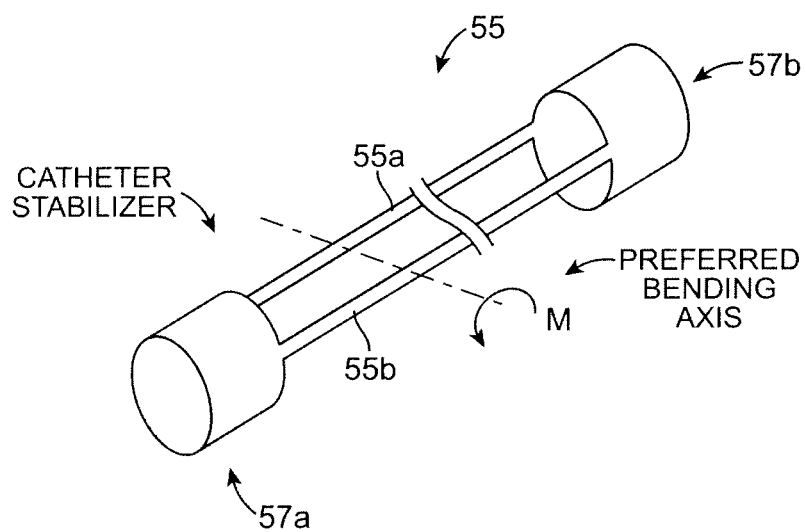
FIG. 14 is a third embodiment of the spine of FIG. 12 showing a pair ribs located on the sides of the spine.
Figure 15:
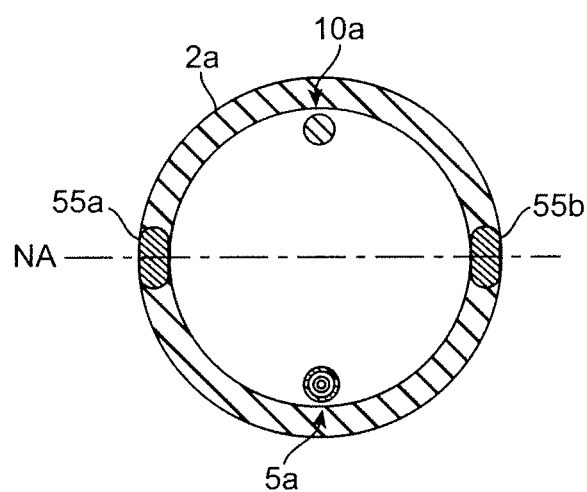
FIG. 15 is cross-sectional view of the distal end of a second embodiment of a catheter shaft configured to optimize the Needle Extension Accuracy and Repeatability (NEAR) for the catheter. This embodiment includes a spine similar to that shown in FIG. 14 and further re-locates a needle assembly and tendon assembly of the catheter of FIG. 1 to optimize NEAR and improve controllability of the distal end of the catheter shaft.

An alternative embodiment for a spine is depicted in FIG. 14. In this embodiment a spine 55 includes opposing ribs 55a, 55b centered on a preferred axis for bending. As will be appreciated, ribs 55a, 55b are wider over the sheath 2a circumference than parallel to the bending axis for purposes of maximizing shaft 2a lumen space and reduced outer profile. This desire to maximize lumen space, however, should be balanced against the need to avoid an unstable bending condition when the member 50 is subjected to the bending moment as shown in FIG. 14. Ribs that extend along the circumference of shaft 2a may be susceptible to kinking or buckling, i.e., loads carried more by transverse shearing action than simple bending. To account for this possibility, stiffeners 55a, 55b may be rounded or additional structure added (e.g., as shown in FIG. 15) to promote simple bending (as opposed to twisting, kinking, shear-bending or predominantly shear). In some embodiments the struts may have rounded edges or be completely circular, or a wire may be added to improve strength for the applied bending moment. In other embodiments, simple bending may be promoted by reducing the height to width ratio of the strut geometry.

Figure 16:
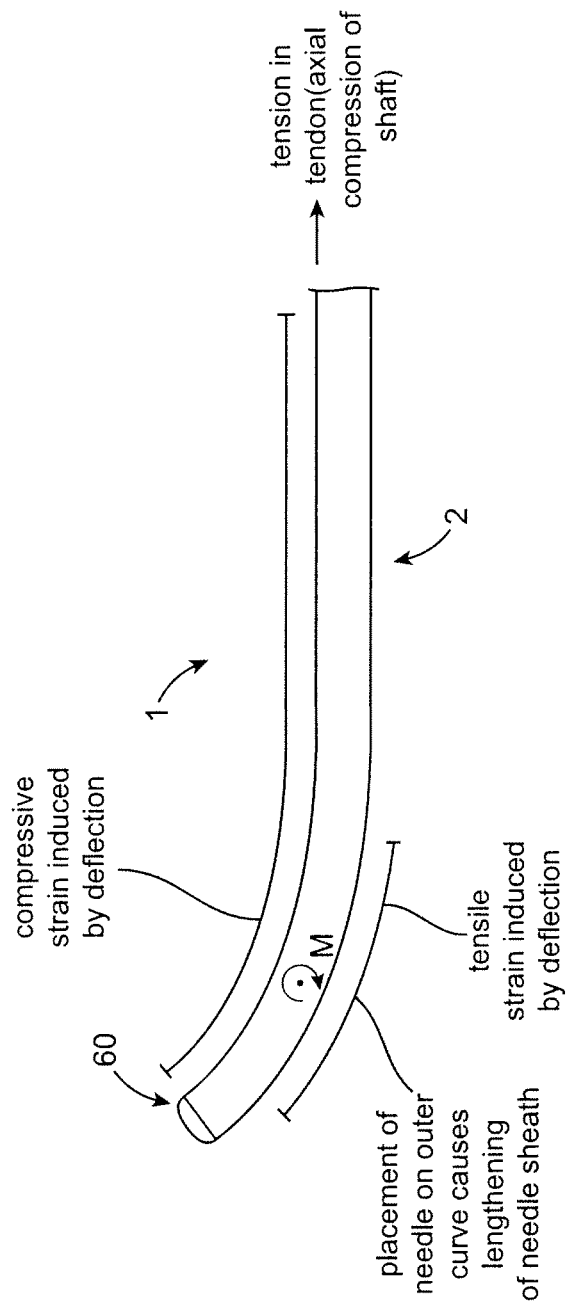
FIG. 16 is a side view of a portion of the catheter shaft near and including the distal end for the embodiment of FIG. 15. This figure illustrates strain properties in a deflected shaft relating to NEAR.

FIG. 15 shows a cross-section of an embodiment of the distal end 6 adopting the spine 55 of FIG. 14, modified to include rounded struts 55. According to this embodiment, the tendon 10a is preferentially located along an axis that is perpendicular to the preferred bending axis, or the NA. Placement of the tendon 10a along the periphery of the spine 50 will increase the moment arm (L, FIG. 10-11). Thus, there can be provided improved steering of the tip 60. Also, as mentioned earlier, the greater the moment arm the less force is needed for deflection, which reduces the amount of compression of the proximal shaft or relative movement between the tip and needle 5a. FIG. 16 shows a side view of the catheter 1 when the tendon 10a is placed in tension. For purposes of this discussion, the effect of this deflection may be described in terms of the stress/strain resulting from the clockwise bending moment M drawn in FIG. 16.

The embodiment depicted in FIGS. 15-16 intentionally places the needle assembly 5 away from the NA. In particular, the needle assembly 5 is placed in a region of tensile strain (lower end in FIG. 16) resulting from the applied moment. The region of tensile strain can counteract the axial compression in the shaft 2 resulting from the tendon 10a being pulled towards the proximal end 4 of the catheter 1.

As mentioned earlier, in regards to the axial compression of the shaft when the tendon 10a is pulled, the needle 5a, being axially uncoupled to the needle sheath or other structure will not shorten. The needle sheath 5b and tip, however, will shorten. A marker, typically located at the tip, therefore will move relative to the needle. A negative effect on NEAR occurs.

In order to counterbalance this effect, the needle 5a may be placed along the lateral edge of the catheter subjected to tensile strain in bending, i.e., opposite the end of where the tendon 10a is located, to compensate for the effects of axial compression of the shaft section 4. In essence, the needle sheath 5b is located in an area where components are elongated due to bending, so that the effects of shaft compression are negated, or at least compensated for to some extent. As a result, with appropriate design of the needle sheath 5b location and device components, a zero net length change of the needle sheath 5b (hence the exit point for the needle 5a at the tip) may be obtained. The location of a tip marker, or other reference point on the catheter, relied on by an operator to locate the exit point for the needle, should therefore remain unchanged relative to the location of the needle tip, regardless of whether, or the degree of deflection of the distal end. This design is expected to be an optimization of NEAR.

Securing the Distal Tip

According to another aspect of the disclosure the tip 60 of the steering catheter 1 may be constructed to form a positive mechanical engagement to the catheter shaft 2a or deflection spine 50. Referring once again to FIG. 1, the tip 60 is typically bonded to the catheter body by, e.g., adhesive welding, thermal welding, etc. One example of such a device is an angioplasty balloon in which the tip of the catheter is thermally welded to the inner wall of the catheter.

Figure 17A:
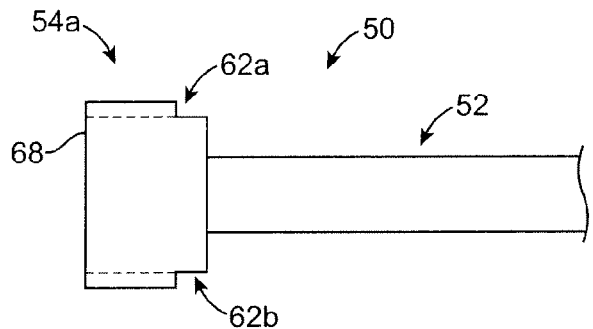
FIGS. 17A-17B and 18A-18B are side views of a catheter tip and spine assembly according to another aspect of invention. According to these embodiments, a tip and distal stabilizer portion of a spine are configured to interlock, thereby forming an interfering mechanical engagement.
Figure 17B:
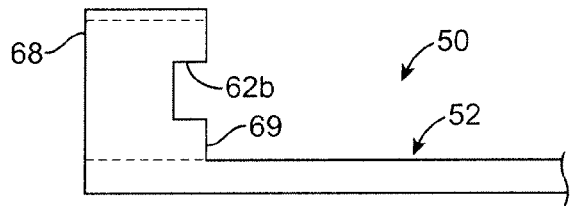
Figure 18A:
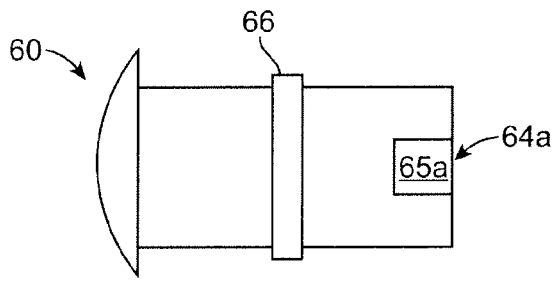
Figure 18B:
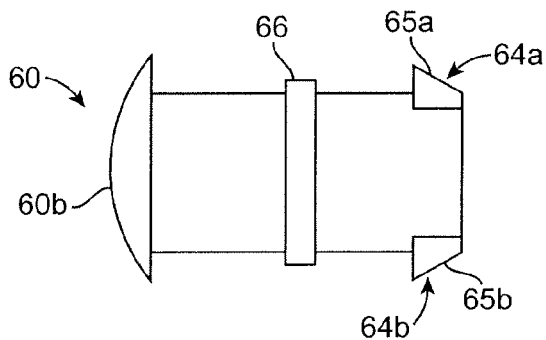
Figure 19:
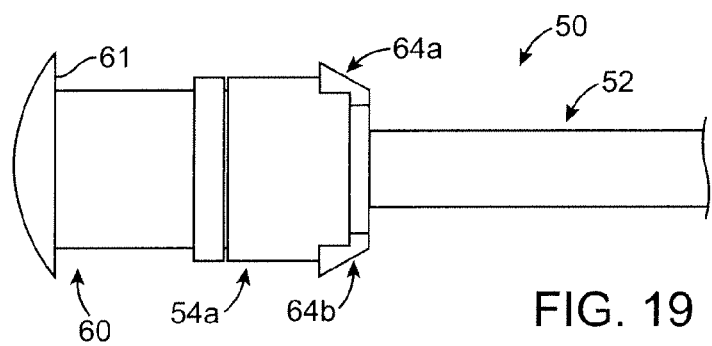
FIG. 19 is a side view of a portion of the assembled spine and tip of FIGS. 17-18.

Referring to FIGS. 17-19, a distal portion of a deflective spine 50 and tip 60 according to one embodiment of a distal tip assembly is described. In this embodiment the distal stabilizer 54a is modified to form notches 62a and 62b, as depicted in FIG. 17A and 17B (FIGS. 17A and 17B are rotated 90 degrees relative to each other). The stabilizer 54a has a distal abutting wall 68 having an interior clearance sized to forcibly receive a portion of the tip 60.

FIGS. 18A and 18B side views (90 degree rotation, as in FIGS. 17) of the tip 60 is depicted. The proximal end of the tip 60 includes a pair of chamfers 64a, 64b having sloped surfaces 65a, 65b. An annular ridge, or stop 66 is formed distal of the chamfers 64 to serve as an abutting surface for the front wall 68 of the stabilizer 54a. It will be appreciated that the chamfers may have alternative shapes such as cylindrical, non-tapered, semi-circular, or any other shape that allows it to interface with a mating snap groove in a locking or interfering manner. In the embodiment depicted in FIGS. 17-19 the tip 60 and stabilizer 54 are mated by forcing the pin through the clearance until the trailing edge of the sloped surface 65 clears the grooves 62 formed in the stabilizer 54. Thus, the assembled piece depicted in FIG. 19, which shows that the tip 60 is held by an interfering mechanical engagement to the stabilizer 54 of the deflection spine 50, is assembled in the following manner. The chamfers engage the wall 68. Due to the sloped surface, the wall of the stabilizer will deform elastically outwardly as the tip 60 is forced through the stabilizer. Once the chamfers have cleared the grooves 62, the stabilizer will snap back to its original shape. The straight, distal edge of the chamfer prevents dislodgment of the tip 60 from the spine 50 when the assembly is placed in tension and stabilizer engagement with stop 66 prevents dislodgement of tip 60 when the assembly is place in compression. Moreover, the grooves will prevent rotation of the tip relative to the stabilizer. Thus, the tip 60, where normally the distal end of the tendon is attached to the tip and the tendon is inserted into the tendon sheath, may be joined to the catheter without significant rotational forces applied to the tendon bond to the tip, without the polymer damaging high heat of welding and without the possibility of adhesive entering the tendon sheath to interfere with the deflection of the catheter tip.

Figure 20:
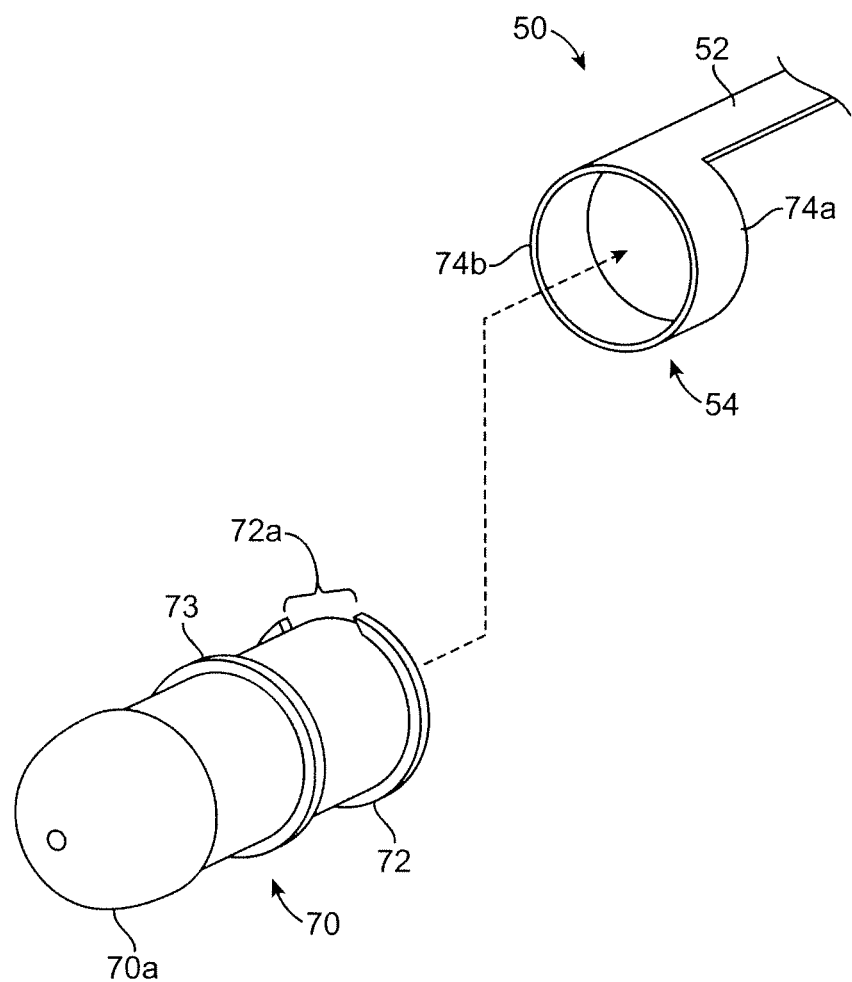
FIG. 20 is an exploded perspective view of a second assembly for the distal tip and distal stabilizer of the spine.
Figure 21:
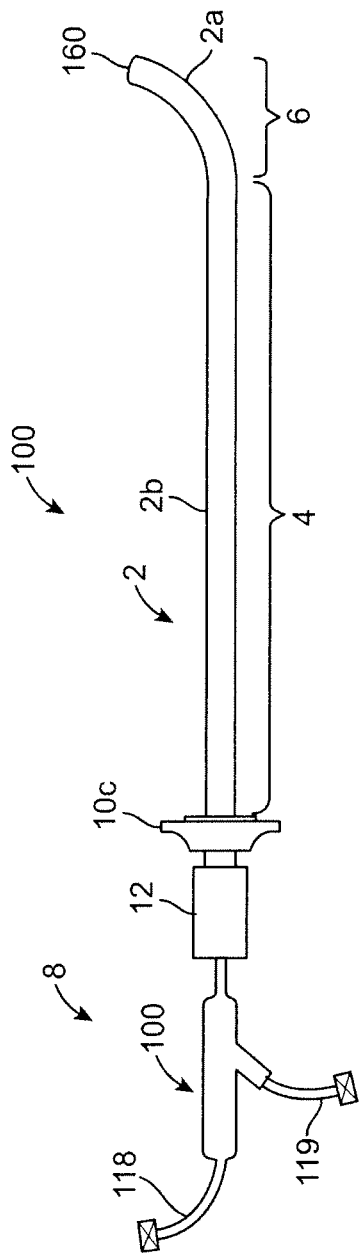
FIG. 21 shows a side view of another embodiment of an agent delivery catheter. This embodiment of a catheter is configured to deliver a therapeutic to a target tissue without using a puncturing needle, as in the case of the catheter of FIG. 1.
Figure 22:
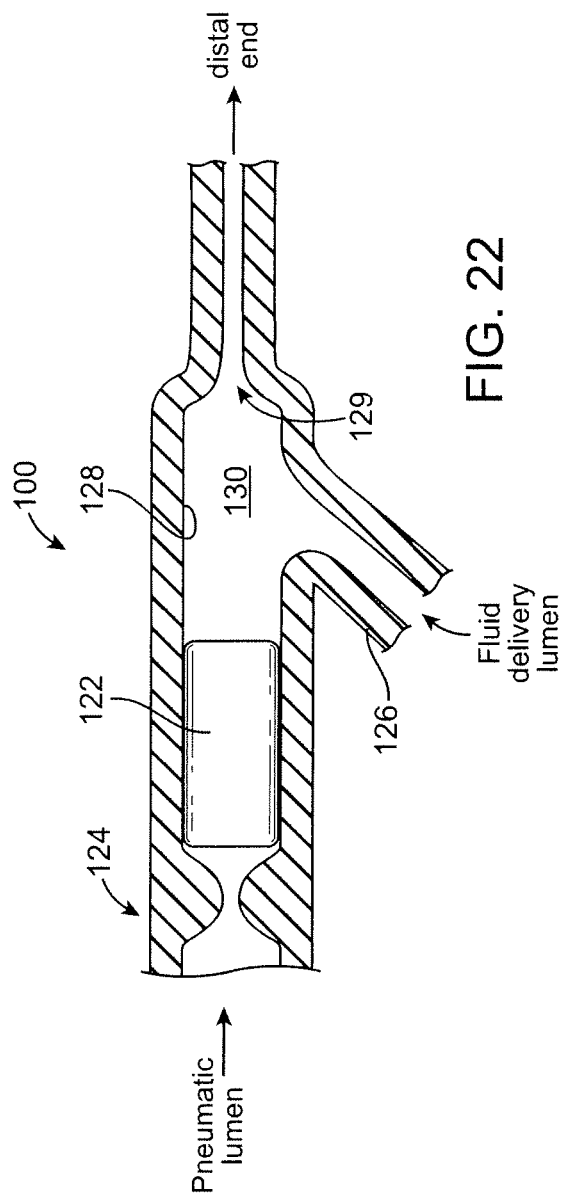
FIG. 22 shows a partial cross-sectional side view schematic of a pneumatic delivery device for the catheter of FIG. 23.

FIG. 20 is an exploded assembly view of a second embodiment. In this embodiment a tip 70 having a distal end 70a includes a first annular ridge 73 and spaced proximal, second annular ridge 72. Similar to the embodiments discussed in connection with FIGS. 17-19 the abutting surfaces of ridges 72 and 73 define a spacing that will form an interference fit with the mating walls of the stabilizer 54. In this embodiment, however, an annular ridge is used, as opposed to chamfers spaced to align with grooves.

Ridge 72 includes a gap 72a sized to receive the rib 52 of the spine 50 when the gap 72a is aligned with the rib 52. Assembly of the second embodiment may proceed as follows. First, the proximal end of the tip 70 is forced through the annular stabilizer 54 clearance provided by the spine 50. The annular ridge 72 may include a chamfer-like leading edge (as in the first embodiment) to facilitate elastic expansion of the stabilizer of the spine 50 as the annular ridge 72 is forced through the annular passage of the stabilizer 54. Once the ridge 72 reaches its abutting wall 74a of the stabilizer 54, the stabilizer 54 will snap into place between the opposing walls of 72, 73 (thereby forming an interference fit) as before, provided the gap 72a is aligned with the rib 52. If it is not aligned, then the tip 70 may simply be rotated in this engagement position until the gap 72a aligns, at which point the rib 52 falls into the gap 72a. Again, one advantage of the design is that relative rotation between the shaft and tip 60 is avoided.

It will be appreciated that these design features may be utilized on other portions of the device. For example, it may be desirable to secure the distal tip 60, 70 to the distal jacket, in which case the snap features can be used on both of those components to facilitate a locking engagement of the components. Additionally, the snap lip on the distal tip and the snap groove on the deflective spine may be interchanged.

Agents Delivered w/o Needles

Figure 23:
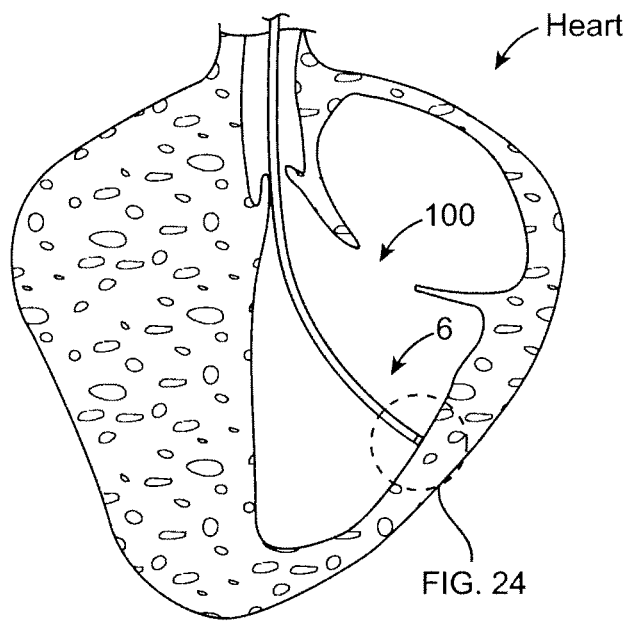
FIGS. 23-24 are schematic drawings of the distal end of the catheter of FIG. 22 within the left ventricle of a patient. The drawings depicts the tip of the catheter located at a target tissue site.

According to another aspect of the disclosure an agent delivery catheter is provided that does not use a needle to deliver agent to a target tissue. FIG. 23 shows one such catheter. The catheter embodies many of the same features as catheter 1.

Cather 100 includes a shaft 2 having a proximal portion 4 and distal portion 6. The distal portion 6 (shown here in a deflected position) includes a tip 160 configured to deliver agent to an agent tissue without using a sharpened needle. The control portion 8 for the catheter 100 includes a steering guide 10c and steering control 12, as in the case of catheter 1.

In addition to catheter tip steering/guide portions of the control 8, the catheter 100 includes at least two fittings 119 and 118, and a pneumatic fluid delivery device 120. Fitting 119 has an agent delivery fitting for connecting to a therapeutic agent source. The second fitting 118 may be used for connecting to a pneumatic source, such as a compressed air line.

Figure 24:
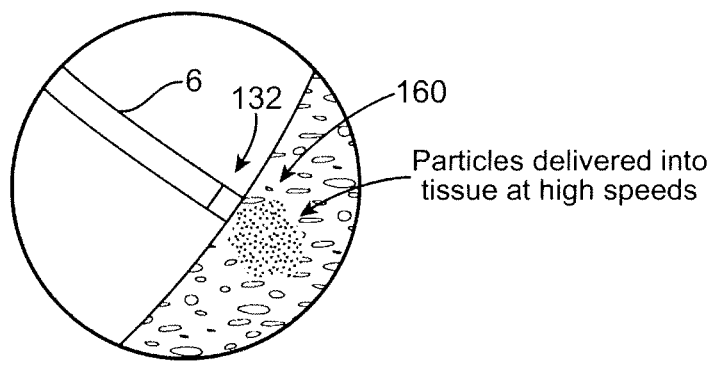

FIG. 24 diagrams the basic construction for the pneumatic delivery device 120. It is a cross-sectional view of the device 120 show in FIG. 23. The device is configured for delivering agent at high momentum through the body of the catheter shaft 2 towards the tip 160. A pneumatically driven mechanism (not shown in its entirety in FIG. 24) is coupled to a firing pin or drive pin 122. When activated, the pin 122 is propelled at high speeds from its position shown in FIG. 24 towards the channel disposed above and to the right of the fluid delivery lumen 126. The pneumatically driven mechanism introduces a shock wave into a fluid column by way of the pneumatically driven pin 122, thereby driving a fluid column at high speeds for very short duration from the distal end 160 of the catheter (left to right in FIG. 24). The fluid delivery lumen 126 is in fluid communication with the fluid fitting 119 and may be used for introducing a therapeutic agent from a syringe or other source. A pneumatic lumen 124 is in fluid communication with a pneumatic fitting via fitting 118, and is capable of delivering compressed gas into the pneumatically driven mechanism. Drive pin 122 is positioned within a fluid channel 130 of the drive mechanism. The fluid channel 130 is in fluid communication with both the pneumatic lumen 124 and the fluid delivery lumen 126.

When the drive pin 122 is in a proximal position (FIG. 24), therapeutic agent may be transported through the fluid delivery lumen 126 and into a lumen of the catheter shaft 2 toward the catheter tip 160. When the drive pin 122 is in a distal position, the fluid delivery lumen 126 is obstructed by the drive pin 122, which prevents additional therapeutic agent from being injected by the syringe or other fluid source.

The drive pin 122 can be moved rapidly from the proximal to the distal position under the force of the pneumatic pressure. A separate trigger mechanism (not shown) may be used to control the application of pneumatic pressure. When the drive pin 122 is driven forward rapidly, it introduces a shock wave within the fluid column that it is plunged against. This shock wave travels throughout the catheter lumen and displaces a small volume of fluid from the catheter tip at a very high speed. At the distal end a check or one-way valve may be constructed at the tip 160 so that fluid flows outward under the pressure force of the fluid column, then closes. A hypotube is preferred for the fluid delivery lumen, as this will cause a more metered release of injectate than a tube made of a visco-elastic material.

Since the fluid may be a solution of particles containing a therapeutic agent, the particles will be ballistically delivered into the tissue to a depth that is dependent on their mass, the tissue consistency, and the speed at which they are delivered. This depth of delivery can be designed precisely using well known principles of physics.

FIG. 25 shows catheter 100 with distal end 6 placed within the left ventricle of a patient. After tracking the catheter to the appropriate location, the tip 160 is preferably placed against the myocardial wall adjacent to the target treatment zone. Catheter tip 160 position may be verified through a radiopaque marker 132 or by using position sensing features such as EKG or other sensors, such as ultrasound.

Referring to FIG. 26, after placing the catheter tip 160 against the myocardial wall, therapeutic agent may be introduced into the fluid delivery lumen. The therapeutic agent is preferably introduced until a complete fluid column is formed in the catheter lumen. This will ensure that the impending shock wave will transmit fully through the column and create the particle delivery into the myocardial tissue.

After the fluid delivery lumen 126 is primed and the catheter tip 160 is disposed on or adjacent the myocardial wall, the pneumatic source may be activated to actuate the drive pin 122, thereby forming a shock wave within the fluid column and propelling therapeutic agent particles into the target tissue, as shown.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A catheter configured for controlled whipping in rotational increments, wherein a portion of the catheter is forced to assume a curved shape in a patient's vasculature to position a distal portion in an operative position for performing a medical procedure, comprising:
    an elongated tubular shaft having proximal and distal shaft portions, and a lumen therein, the proximal shaft portion configured for transmitting a torque from the proximal shaft portion to the distal shaft portion;
    a first section of the proximal shaft portion having a first flexural modulus; and
    a second section of the proximal shaft portion having circumferentially spaced voids, each of which extending lengthwise over the second section;
    wherein the second section is such that the flexural modulus of the second section would be substantially higher than the first flexural modulus if the voids were not formed in the second section; and
    wherein the second section occupies a position along the proximal shaft portion that substantially assumes the curved shape.

2. The catheter of claim 1, wherein the second section is made from a material having a higher modulus of elasticity than the material used to form the first section.

3. The catheter of claim 1, wherein the voids are formed so that the second section has a first flexural modulus when the second section assumes a first curved shape, and a second flexural modulus when the second section forms a second curved shape, the first and second modulus being different from each other.

4. The catheter of claim 3, wherein the first curved shape has a lower curvature than the curvature of the second curved shape and the first flexural modulus is lower than the second flexural modulus.

5. The catheter of claim 4, wherein the second section is made from a metal and the second section is made from a polymer or composite including a polymer.

6. The catheter of claim 1, further comprising a tendon configured to bend the elongate tubular shaft about a bending axis, and the second section having the circumferentially spaced voids is disposed axially between the bending axis and a proximal end of the proximal shaft portion.

7. The catheter of claim 1, further comprising a compression cage having a deflection spine extending axially within the elongate tubular shaft and configured to prevent kinking of the elongate tubular shaft, the deflection spine having distal and proximal ends, and the first section having the circumferentially spaced voids is disposed axially between a proximal end of the deflection spine and a proximal end of the proximal shaft portion.

8. The catheter of claim 1, wherein the second section comprises a tube having a lumen and a wall surrounding the lumen, and the wall comprises circumferential sections that vary with each other in flexural rigidity.

9. The catheter of claim 8, wherein a plurality of voids formed on a surface of the wall provides the circumferential sections with the variable flexural rigidity.

10. The catheter of claim 8, wherein the wall when viewed in cross-Section has a plurality of axes of symmetry that is finite in number.

11. The catheter of claim 1, further comprising a needle shaft disposed within the lumen of the elongate tubular shaft.

12. An agent delivery catheter configured to improve needle accuracy and repeatability when the catheter assumes a curved shape, comprising:
    an elongate shaft including a proximal end and a distal end;
    a tendon disposed within a shaft lumen of the elongate shaft, affixed to the distal end, and offset from a neutral axis of the distal end to enable deflection of a distal tip of the elongate shaft by pulling the tendon towards the proximal end; and
    a needle shaft disposed within the shaft lumen and located approximately coincident with the neutral axis.

13. The agent delivery catheter of claim 12, whereby the neutral axis is defined as the plane having zero strain when the catheter shaft is deflected, whereby compressive strain is located above the neutral axis and tensile strain is located below the neutral axis.

14. The agent delivery catheter of claim 12, wherein the needle is enclosed within a sheath and the sheath has a much lower axial stiffness than the needle.

15. An agent delivery catheter configured to improve needle accuracy and repeatability when the catheter assumes a curved shape, comprising:
  an elongate shaft including a proximal end and a distal end, the shaft being pre-disposed to deflect in a first direction so that a first region of the elongate shaft is placed in tension and a second region of the elongate shaft is placed in compression;
  a tendon disposed within the shaft lumen and affixed to the distal end, the tendon being offset from a neutral axis to enable deflection of a distal tip of the elongate shaft by pulling the tendon towards the proximal end, whereby the pulling on the tendon compresses the catheter; and
  a needle disposed within the shaft lumen, the needle being located in the portion of the first region that negates the compression induced by the tendon.

16. The agent delivery catheter of claim 15, wherein the distal end has a luminal space, that, when viewed in cross-section
  the neutral axis passes through the center of the cross-section,
  a pair of stiffening ribs are disposed on opposite sides and lie approximately along the neutral axis,
  the needle is spaced from the neutral axis and the stiffening ribs, and
  the tendon is spaced from the neutral axis, the stiffening ribs and the needle,
  wherein the needle and the tendon pass through opposite sides of the neutral axis.

17. The agent delivery catheter of claim 15, further including a deflection spine disposed within the lumen of the shaft at the distal end and configured for increasing the axial stiffness of the distal end, the deflection spine having a first and second rib extending parallel and approximately coincident with the neutral axis, the first and second ribs being fixed to a distal and proximal stabilizer.

18. A method for improving the needle accuracy and repeatability for an agent delivery catheter, comprising the steps of:
  providing a catheter including a shaft having a distal and a proximal end, a tendon assembly disposed within the shaft and configured to deflect the distal tip when the tendon is loaded by an operator at the proximal end, whereby the deflected state of the shaft creates a compressive strain region and a tensile strain region, and the loaded tendon produces a net axial compression on the shaft; and
  placing a needle assembly in a tensile strain region caused by the deflection such that the elongation caused by the deflection negates the net compression caused by the loaded tendon,
  wherein the needle assembly includes a needle sheath and a needle within the needle sheath, and the needle sheath is capable of changing length when subjected to compression and tension, and the placing a needle assembly in a tensile strain region caused by the deflection includes placing the needle assembly in a portion of the tensile strain region at which there is a zero net length change of the needle sheath when the shaft is in the deflected state.

19. The method of claim 18, wherein the catheter is intended to assume a curved position in relation to an operative position of the catheter for performing a medical procedure such that the degree of curvature of the shaft and deflection of the distal tip is known or within a known range, such that the placing a needle assembly in a tensile strain region caused by the deflection includes placing the needle assembly in the shaft lumen relative to the degree of curvature of the assumed shape and compression caused by the loaded tendon.

* * * * *